(12) United States Patent
Chehrazi et al.

(10) Patent No.: US 12,073,472 B2
(45) Date of Patent: Aug. 27, 2024

(54) MACHINE-LEARNING DRIVEN DATA ANALYSIS BASED ON DEMOGRAPHICS, RISK, AND NEED

(71) Applicant: Nayya Health, Inc., New York, NY (US)

(72) Inventors: Sina Chehrazi, New York, NY (US); Josh Allen Brown, San Diego, CA (US); Lisa Renee Carpenter, Jackson, WY (US); Akash Magoon, New York, NY (US); Aman Magoon, Fallston, MD (US)

(73) Assignee: Nayya Health, Inc., New York, NY (US)

( * ) Notice: Subject to any disclaimer, the term of this patent is extended or adjusted under 35 U.S.C. 154(b) by 0 days.

(21) Appl. No.: 18/337,628

(22) Filed: Jun. 20, 2023

(65) Prior Publication Data

US 2023/0334590 A1 Oct. 19, 2023

Related U.S. Application Data

(63) Continuation of application No. 17/401,596, filed on Aug. 13, 2021, now Pat. No. 11,720,973, which is a
(Continued)

(51) Int. Cl.
*G06Q 40/08* (2012.01)
*G06N 20/00* (2019.01)
(Continued)

(52) U.S. Cl.
CPC ............. *G06Q 40/08* (2013.01); *G06N 20/00* (2019.01); *G06Q 30/0203* (2013.01); *G16H 10/60* (2018.01)

(58) Field of Classification Search
CPC .............................. G06Q 40/08; G16H 10/60
See application file for complete search history.

(56) References Cited

U.S. PATENT DOCUMENTS 7,305,347 B1 12/2007 Joao
7,711,660 B1 5/2010 Gentile et al.
(Continued)

FOREIGN PATENT DOCUMENTS

CN 109545317 A 3/2019
EP 3401847 A1 11/2018
(Continued)

OTHER PUBLICATIONS

Malhotra et al.; "Machine Learning in Insurance"; Accenture; 2018; pp. 1-13; located at https://www.accenture.com/_acnmedia/pdf-84/accenture-machine-leaning-insurance.pdf.
(Continued)

*Primary Examiner* — Scott C Anderson
(74) *Attorney, Agent, or Firm* — NovoTechIP International PLLC

(57) ABSTRACT

A data processing system for recommending insurance plans implements obtaining an electronic copy of demographic information associated with a user; analyzing the demographic information with a first machine learning model to recommend a bundle of insurance policies based on the demographic information, wherein the first machine learning model is configured to group insured people having similar demographics into clusters and to generate the bundle of insurance policies based on predicted medical insurance consumption associated with a respective group into which the model predicts that the first user falls; customizing the recommended bundle of insurance policies based on the demographic information associated with the user to generate a customized bundle of insurance policies; generating an insurance recommendation report that pres-
(Continued)

ents the customized bundle of insurance policies to the user; and causing a user interface of a display of a computing device associated with the user to present the insurance recommendation report.

20 Claims, 23 Drawing Sheets

Related U.S. Application Data continuation of application No. 17/229,020, filed on Apr. 13, 2021, now Pat. No. 11,113,770.

(51) Int. Cl.
*G06Q 30/0203* (2023.01)
*G16H 10/60* (2018.01)

(56) References Cited

U.S. PATENT DOCUMENTS

| | | |
|---|---|---|
| 7,853,459 B2 | 12/2010 | Kay |
| 8,185,463 B1 | 5/2012 | Ball |
| 8,412,537 B1 | 4/2013 | Fenton et al. |
| 8,712,797 B1 | 4/2014 | Bezdek et al. |
| 8,930,228 B1 | 1/2015 | Ball |
| 9,183,593 B2 | 11/2015 | Willis et al. |
| 9,495,700 B2 | 11/2016 | Hoch et al. |
| 9,773,094 B1 | 9/2017 | Balagere et al. |
| 10,395,006 B2 | 8/2019 | Brown |
| 10,402,908 B1 | 9/2019 | Ross et al. |
| 10,803,528 B2 | 10/2020 | Mdeway |
| 10,810,223 B2 | 10/2020 | Sundararaman et al. |
| 10,818,395 B1 | 10/2020 | Khalak et al. |
| 11,113,770 B1 | 9/2021 | Magoon et al. |
| 11,120,510 B1 | 9/2021 | Mitchell et al. |
| 11,170,450 B1 | 11/2021 | Magoon et al. |
| 11,244,370 B2 | 2/2022 | Ketchel, III et al. |
| 11,720,973 B2 | 8/2023 | Chehrazi et al. |
| 11,763,393 B2 | 9/2023 | Chehrazi et al. |
| 2004/0111302 A1 | 6/2004 | Falk et al. |
| 2005/0203828 A1 | 9/2005 | Lyakovetsky |
| 2006/0173715 A1 | 8/2006 | Wang |
| 2009/0281841 A1 | 11/2009 | Basak et al. |
| 2009/0287509 A1 | 11/2009 | Basak et al. |
| 2011/0046985 A1 | 2/2011 | Raheman |
| 2013/0046624 A1 | 2/2013 | Calman et al. |
| 2014/0278495 A1 | 9/2014 | Rourke et al. |
| 2015/0006206 A1 | 1/2015 | Mdeway |
| 2015/0046088 A1 | 2/2015 | Jang et al. |
| 2015/0142479 A1 | 5/2015 | Porter et al. |
| 2016/0042148 A1 | 2/2016 | Bradley |
| 2017/0140114 A1 | 5/2017 | Are et al. |
| 2018/0089379 A1 | 3/2018 | Collins et al. |
| 2019/0005198 A1 | 1/2019 | Richards et al. |
| 2019/0042887 A1 | 2/2019 | Nguyen et al. |
| 2019/0080416 A1 | 3/2019 | Smith et al. |
| 2019/0266243 A1 | 8/2019 | Farooq et al. |
| 2019/0348180 A1 | 11/2019 | Sharifi Sedeh |
| 2019/0384849 A1 | 12/2019 | Sundararaman et al. |
| 2020/0020038 A1 | 1/2020 | Haile et al. |
| 2020/0043070 A1 | 2/2020 | Ketchel, III et al. |
| 2020/0096353 A1 | 3/2020 | Misaki et al. |
| 2020/0105392 A1 | 4/2020 | Karkazis et al. |
| 2020/0279025 A1 | 9/2020 | Owen |
| 2020/0364797 A1 | 11/2020 | Halpern-Manners et al. |
| 2020/0410601 A1 | 12/2020 | Laumeyer et al. |
| 2021/0035224 A1 | 2/2021 | Crabtree et al. |
| 2021/0035225 A1 | 2/2021 | Simpson et al. |
| 2021/0065132 A1* | 3/2021 | Yang ..................... G06Q 40/08 |
| 2021/0065862 A1 | 3/2021 | Siegel |
| 2021/0074401 A1 | 3/2021 | Bezdek et al. |
| 2021/0090191 A1* | 3/2021 | Chan ..................... G16H 40/67 |
| 2021/0103829 A1 | 4/2021 | Barshan et al. |
| 2021/0125287 A1* | 4/2021 | Fasoli .................. G06Q 20/227 |
| 2021/0210185 A1 | 7/2021 | Allred et al. |
| 2021/0312515 A1 | 10/2021 | Ketchel, III et al. |
| 2022/0012766 A1 | 1/2022 | Hinton, II |
| 2022/0019913 A1 | 1/2022 | Ayyadevara et al. |
| 2022/0094699 A1 | 3/2022 | Birur |
| 2022/0101162 A1 | 3/2022 | Palacios et al. |
| 2022/0327584 A1 | 10/2022 | Magoon et al. |
| 2022/0327585 A1 | 10/2022 | Magoon et al. |
| 2022/0366474 A1 | 11/2022 | Kuhn et al. |
| 2023/0410211 A1 | 12/2023 | Chehrazi et al. |

FOREIGN PATENT DOCUMENTS

| | | |
|---|---|---|
| WO | 2005076957 A2 | 8/2002 |
| WO | 2008057761 A3 | 5/2008 |
| WO | 2014209517 A1 | 12/2014 |
| WO | 2015024251 A1 | 2/2015 |
| WO | 2016138102 A1 | 9/2016 |
| WO | 2018156942 A1 | 8/2018 |
| WO | 2018166853 A1 | 9/2018 |

OTHER PUBLICATIONS

Sahu et al.; "Automating claims adjudication workflows using Amazon Textract and Amazon Comprehend Medical"; AWS for Industries; Nov. 19, 2019; pp. 1-11; located at https://aws.amazon.com/blogs/industries/automating-claims-adjudication-workflows-using-amazon-textract-and-amazon-comprehend-medical/.
International Search Report and Written Opinion for PCT/US2022/023491 dated Jul. 18, 2022, 10 pages.
International Search Report and Written Opinion for PCT/US2022/023512 dated Jul. 13, 2022, 10 pages.
Non-Final Office Action issued Feb. 4, 2022 in corresponding U.S. Appl. No. 17/472,167.
Final Office Action issued Jun. 1, 2022 in corresponding U.S. Appl. No. 17/472,167.
Non-Final Office Action issued Feb. 21, 2023 in corresponding U.S. Appl. No. 17/472,167.
Final Office Action issued Jul. 19, 2023 in corresponding U.S. Appl. No. 17/472,167.
Notice of Allowance issued May 2, 2023 in U.S. Appl. No. 17/499,485.
International Search Report and Written Opinion for PCT/US2022/023499 dated Jul. 18, 2022, 11 pages.
Notice of Allowance issued Jun. 17, 2021 in corresponding U.S. Appl. No. 17/229,020.
Notice of Allowance issued Mar. 20, 2023 in corresponding U.S. Appl. No. 17/401,596.
Non-final Office Action issued Jan. 31, 2022 in U.S. Appl. No. 17/472,029.
Final Office Action issued Jun. 7, 2022 in U.S. Appl. No. 17/472,029.
Final Office Action issued Sep. 7, 2023 in U.S. Appl. No. 17/472,029.
Non-final Office Action issued Jan. 26, 2023 in U.S. Appl. No. 17/472,029.
International Search Report and Written Opinion for PCT/US2022/023502 dated Jul. 15, 2022, 10 pages.
Non-final Office Action issued Jun. 10, 2021 in U.S. Appl. No. 17/228,975.
Notice of Allowance issued Sep. 23, 2021 in U.S. Appl. No. 17/228,975.

* cited by examiner

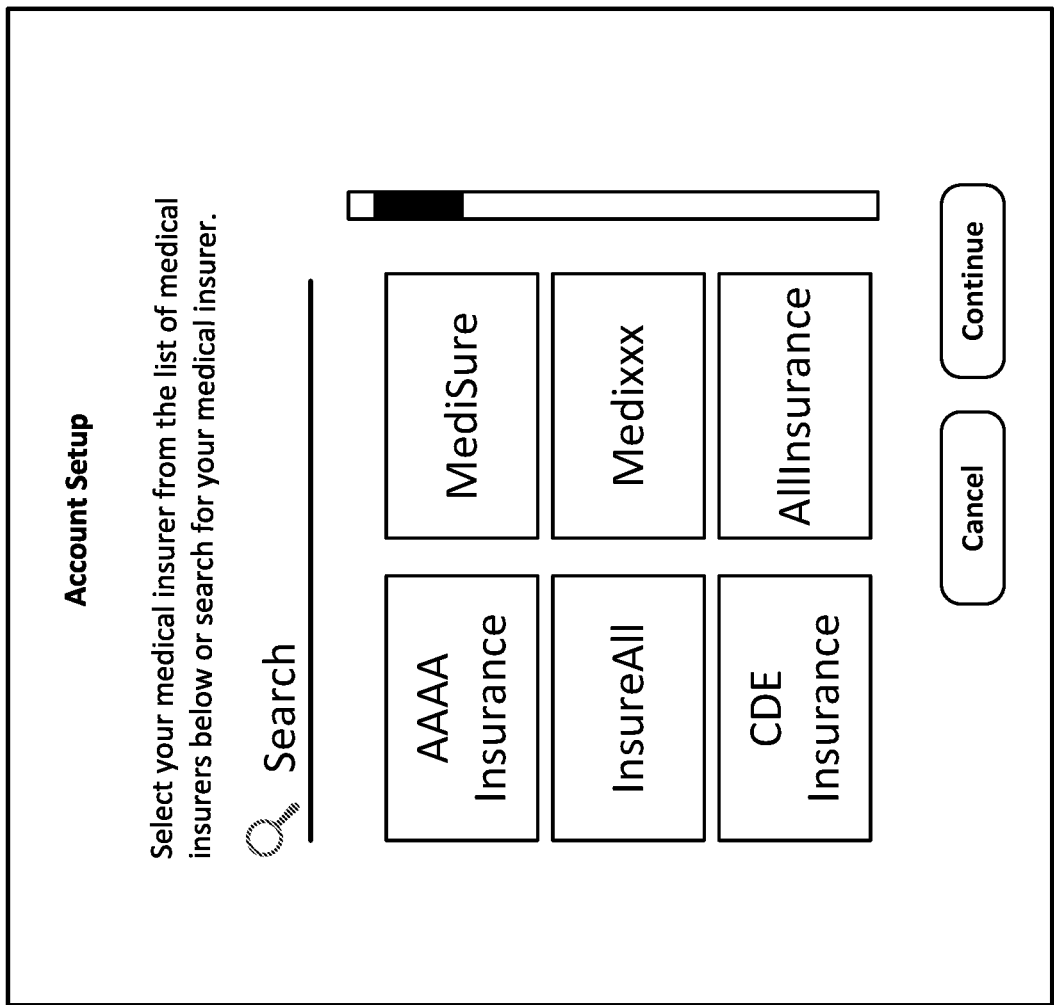

AllInsurance

Where would you like us to send your security code?

○ Text    XXX-XXX-5525

○ Email   tr......@gmail.com

Cancel    Continue

FIG. 5F

AllInsurance

Please verify the security code that was sent to xxx-xxx-5525:

6   1   3
___ ___ ___

6   1   3   3
___ ___ ___ ___

Cancel    Verify

Success

You can now access your policy information and claims for your AllInsurace policy.

[ Close ]

Insurance Dashboard

Anna, we can assess your insurance needs to determine whether your current insurance portfolio meets your needs. Please click "Save now" to begin a short questionnaire so we can gather some information to help assess your needs.

[ Save Now ]

Claims Overview

| Service Date | Member | Type | Provider | Description | You Pay |
|---|---|---|---|---|---|
| Oct 1, 2020 | Jeff | Medical | Dr. Bhatnagar | Orthopedic Consult | $211.50 |
| Sep 23, 2020 | Anna | Dental | Dr. Garcia | Preventative Visit | $25 |
| Sep 23, 2020 | Jeff | Pharmacy | CVS Pharmacy | Prescription | $25 copay |
| Sep 19, 2020 | David | Medical | Dr. Gau | Urgent Care Visit | $412.44 |
| Sep 15, 2020 | Anna | Pharmacy | CVS Pharmacy | Prescription | $10.81 |
| Sep 11, 2020 | Jeff | Medical | Dr. Bhatnagar | Orthopedic Consult | $57.21 |
| Sept 10, 2020 | Jeff | Pharmacy | CVS Pharmacy | Prescription | $10.81 |

Claims Analytics

Costs Overview

Total Spend $684.75

Medical
Pharmacy  15%
Dental  7%

Total Spend $684.75

Medical Breakdown 66%

Specialist Visits  Diagnostics
$41.23  $54.12

Urgent Care  Primary Care
$352.36  $98.64

Inpatient Facility  Outpatient Facility
$97.43  $69.60

FIG. 6A

Insurance Planning Questionnaire

Please answer this short questionnaire so that we can provide you with a recommended insurance plan that fits your needs.

Do you participate in any sports?

☑ Yes

☐ No

Next >

Insurance Planning Questionnaire

Please answer this short questionnaire so that we can provide you with a recommended insurance plan that fits your needs.

Do you participate in any of the following sports? (Select all that apply.)

- ☑ Scuba Diving
- ☑ Rock Climbing
- ☑ Paragliding / Hang Gliding
- ☐ Sky Diving
- ☐ Spelunking / Cave Exploration
- ☑ Base Jumping < Back    Next >

Insurance Planning Questionnaire

Please answer this short questionnaire so that we can provide you with a recommended insurance plan that fits your needs.

Have you experienced any of the following:

- ☑ Fracture/dislocation resulting in a surgury
- ☑ Hospital Admission
- ☑ Ground Ambulance
- ☐ Air Ambulance
- ☐ Fracture/dislocation not resulting in a surgury
- ☑ Physical Therapy < Back    Next >

Insurance Planning Questionnaire

Please answer this short questionnaire so that we can provide you with a recommended insurance plan that fits your needs.

Have there been any changes to your family status in the past year?

- ☑ I got married
- ☐ I had a child
- ☐ I am acting as a caretaker for a parent
- ☐ I can no longer claim a dependent < Back    Next >

Insurance Planning Questionnaire

Please answer this short questionnaire so that we can provide you with a recommended insurance plan that fits your needs.

Is your spouse covered by your medical insurance?

☑ Yes

☐ No

< Back    Next >

Insurance Bundle Recommendation Report

We have put together the following customized insurance plan for you.

(1) Medical Insurance – HMO (Provided by your Employer) – save $250

We recommend that you select the HMO option for your medical insurance when the enrollment period for your medical insurance opens. Switching from the PPO to the HMO option may save you $250 per month to cover both you and your spouse.

(2) Supplemental Accident Insurance - $150 per month

We recommend supplemental accident insurance for you because you participate in extreme sports and medical claims associated with extreme sports are not fully covered by your medical insurance.

(3) Accidental Life Insurance - $200 per month

We recommend accidental life insurance for you because you participate in extreme sports and your existing life insurance policy does not provide coverage for loss of life when engaging in extreme sports. We recommend $250,000 in insurance to provide your spouse < Back    Next >

FIG. 6G

Insurance Bundle Recommendation Report

(1) Medical Insurance – HMO (Provided by your Employer) – save $250

We recommend that you select the HMO option for your medical insurance when the enrollment period for your medical insurance opens. Switching from the PPO to the HMO option may save you $250 per month to cover both you and your spouse. The HMO option is completely covered by your employer.

(2) Supplemental Accident Insurance - $150 per month

We recommend supplemental accident insurance for you because you participate in extreme sports and medical claims associated with extreme sports are not fully covered by your medical insurance.

(3) Accidental Life Insurance - $200 per month

We recommend accidental life insurance for you because you participate in extreme sports and your existing life insurance policy does not provide coverage for loss of life when engaging in extreme sports. We recommend $550,000 in insurance to provide your spouse with the same amount of life insurance that you have in accident-related coverage.

(4) Long-Term Care Insurance - $150 per month

We recommend long-term care insurance for you and your spouse as part of your early retirement planning. Your medical insurance does not cover long-term care, such as assisted living, hospice care, or nursing home care. The premiums for this plan are fixed and the premiums for coverage are lower when obtained at an earlier age and when you are in good health. Both you and your spouse are under age 45 and do not have any major health problems. You may be able to obtain this coverage later Total Cost Projection:

Cost for new coverage:   $500 per month ($6000 per year)

Cost savings:   $250 per month ($3000 per year)

Net Cost:   $250 per month ($3000 per year)

FIG. 10

MACHINE-LEARNING DRIVEN DATA ANALYSIS BASED ON DEMOGRAPHICS, RISK, AND NEED

CROSS-REFERENCE TO RELATED APPLICATIONS

This application claims the benefit of priority from pending U.S. patent application Ser. No. 17/401,596 filed on Aug. 13, 2021, and entitled "Machine-learning driven Data analysis based on demographics, risk, and need", which claims priority from now issued U.S. patent application Ser. No. 17/229,020, filed on Apr. 13, 2021, and issued on Sep. 7, 2021 as U.S. Pat. No. 11,113,770, and entitled "Machine-learning driven Data analysis based on demographics, risk, and need."

BACKGROUND

Determining how much insurance coverage and what types of insurance coverage a person needs can be a confusing and stressful process. An insurance plan may include multiple types of policies which provide coverage for various types of claims, such as but not limited to medical insurance, dental insurance, accident insurance, hospital indemnity insurance, and auto insurance. Each of these policies may cover a variety of different types of claims, and the insured may not have a complete understanding of the minutiae of the coverage provided by each of the policies. The amounts and types of coverage appropriate for a particular person may vary significantly based on the individual needs of that person. Furthermore, the coverage may extend to family members, which may further complicate the decision-making process. As a result, the person may select a plan that may not adequately provide for the needs of the insured. Hence, there is a need for improved systems and methods that provide a technical solution for solving the technical problem of automatically analyzing the insurance needs of a user and providing recommendations to assist the user in building an insurance plan that meets the needs of the user.

SUMMARY

An example data processing system according to the disclosure may include a processor and a computer-readable storage medium storing executable instructions. The instructions when executed cause the processor to perform operations including obtaining an electronic copy of demographic information associated with a user, wherein the demographic information includes first demographic information provided by the user, demographic information obtained from one or more third-party data sources, or both; providing the first demographic information as an input to a first machine learning model; analyzing the first demographic information with the first machine learning model, wherein the first machine learning model is trained to segment people into clusters of people having similar demographics, wherein the first machine learning model is configured to analyze the first demographic information associated with the user to predict and output a cluster associated with the user and output predicted medical spending information associated with the predicted cluster; providing the predicted medical spending information to a recommendation engine to generate a comprehensive insurance plan for the user comprising a plurality of insurance policies based on the predicted medical spending information; customizing the comprehensive insurance plan based on the first demographic information associated with the user to generate a customized bundle of insurance policies; generating an insurance recommendation report that presents the customized bundle of insurance policies to the user; and causing a user interface of a display of a computing device associated with the user to present the insurance recommendation report.

An example method implemented in a data processing system for recommending insurance plans includes obtaining an electronic copy of demographic information associated with a user, wherein the demographic information includes first demographic information provided by the user, demographic information obtained from one or more third-party data sources, or both; providing the first demographic information as an input to a first machine learning model; analyzing the first demographic information with the first machine learning model, wherein the first machine learning model is trained to segment people into clusters of people having similar demographics, wherein the first machine learning model is configured to analyze the first demographic information associated with the user to predict and output a cluster associated with the user and output predicted medical spending information associated with the predicted cluster; providing the predicted medical spending information to a recommendation engine to generate a comprehensive insurance plan for the user comprising a plurality of insurance policies based on the predicted medical spending information; customizing the comprehensive insurance plan based on the first demographic information associated with the user to generate a customized bundle of insurance policies; generating an insurance recommendation report that presents the customized bundle of insurance policies to the user; and causing a user interface of a display of a computing device associated with the user to present the insurance recommendation report.

An example computer-readable storage medium according to the disclosure on which are stored instructions which when executed cause a processor of a programmable device to perform operations of obtaining an electronic copy of demographic information associated with a user, wherein the demographic information includes first demographic information provided by the user, demographic information obtained from one or more third-party data sources, or both; providing the first demographic information as an input to a first machine learning model; analyzing the first demographic information with the first machine learning model, wherein the first machine learning model is trained to segment people into clusters of people having similar demographics, wherein the first machine learning model is configured to analyze the first demographic information associated with the user to predict and output a cluster associated with the user and output predicted medical spending information associated with the predicted cluster; providing the predicted medical spending information to a recommendation engine to generate a comprehensive insurance plan for the user comprising a plurality of insurance policies based on the predicted medical spending information; customizing the comprehensive insurance plan based on the first demographic information associated with the user to generate a customized bundle of insurance policies; generating an insurance recommendation report that presents the customized bundle of insurance policies to the user; and causing a user interface of a display of a computing device associated with the user to present the insurance recommendation report.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The drawing figures depict one or more implementations in accord with the present teachings, by way of example only, not by way of limitation. In the figures, like reference numerals refer to the same or similar elements. Furthermore, it should be understood that the drawings are not necessarily to scale.

FIGS. 5A, 5B, 5C, 5D, 5E, 5F, 5G, and 5H show an example user interface for linking a CAAS account to an insurer account.

FIGS. 6A, 6B, 6C, 6D, 6E, 6F, and 6G show an example user interface for presenting insurance bundle recommendations.

FIG. 10 is a diagram of an example insurance recommendation report.

DETAILED DESCRIPTION

Figure 1:
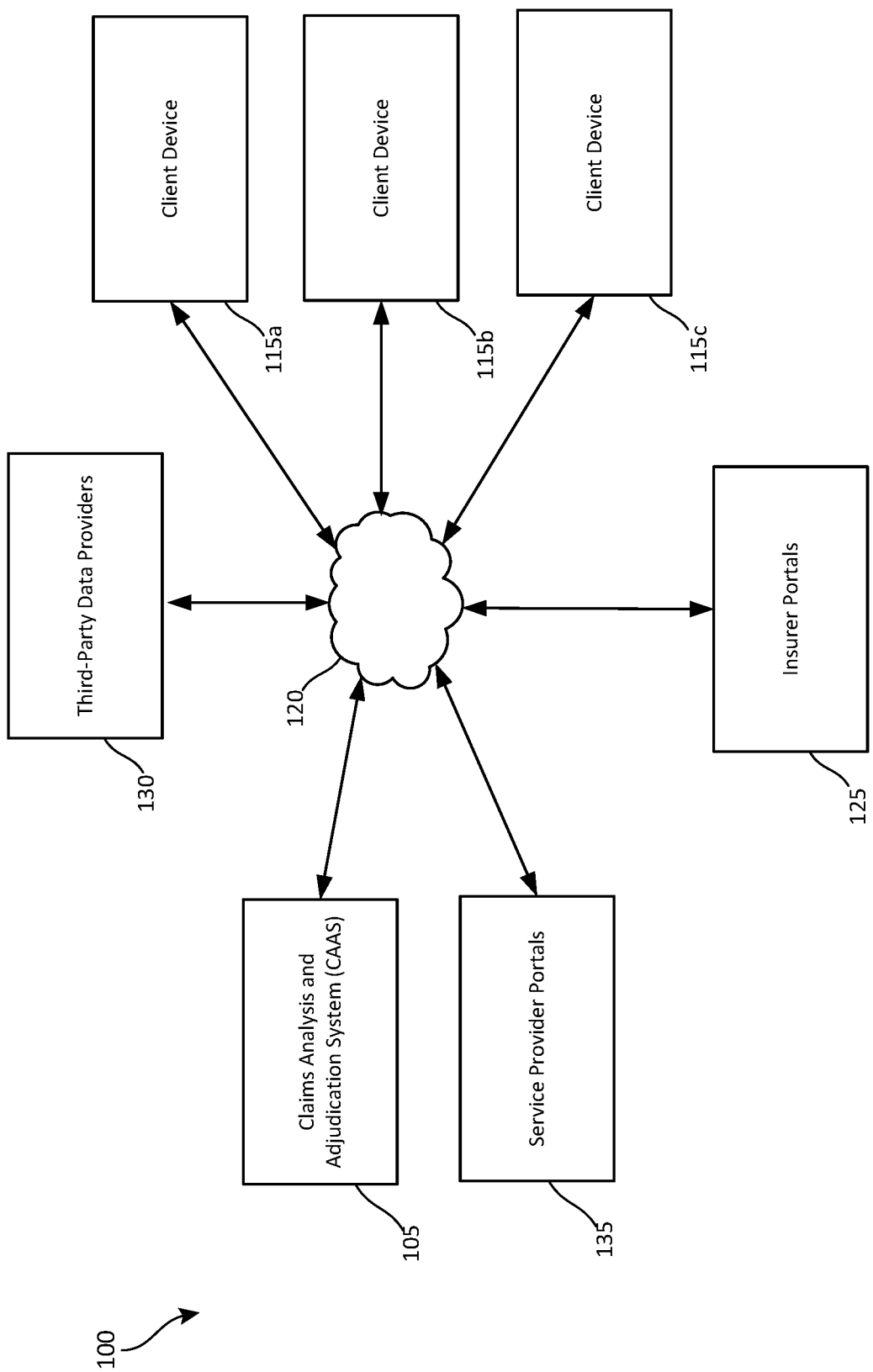
FIG. 1 is a diagram showing an example computing environment in which the techniques disclosed herein may be implemented.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

Techniques are described herein for machine-learning driven recommendation of health and insurance plans that include a bundle of insurance policies based on individual demographics, risk, and needs. Building a comprehensive insurance plan that adequately meets the needs of the insured is a complex process. A plan may include a bundle of insurance policies that each have a complex list of the types of claims that the insurer may cover and the coverage limitations that provide the conditions under which the insurer may cover such claims. To further complicate the process of selecting an appropriate plan, the insured may need to take into consideration the needs of family members who will also be covered by the insurance plan. Furthermore, the insured must take into consideration the cost associated with each type of coverage to ensure that the selected plan meets the financial needs of the user. Understanding how multiple policies may fit together to meet these needs is a confusing and error prone process. The techniques provided herein provide a technical solution to this problem by analyzing demographic information for the user, the risk aversiveness of the user, and the insurance needs of the user using one or more machine learning models to provide recommendations for insurance plans. The one or more machine learning models may be trained using demographic data for an insured population to segment the insured population into clusters of users having similar demographics. The model or models may predict an estimated medical spending for the insured user by predicting a cluster into which the user falls based on the user's demographics and providing the predicted medical spending for that cluster. The predicted medical spending for a cluster may include an amount spent and types of claims typically filed. The predicted medical spending may then be used to create a comprehensive insurance plan for the user that includes a recommended bundle of insurance policies based on the predicted medical spending. The recommended bundle of insurance policies may be customized for the user based on the demographic information of the user, the risk aversiveness of the user, and the needs of the user. A technical benefit of this approach is that the machine learning models may recognize patterns in the insurance consumption and demographic information of the user to recommend a comprehensive insurance plan that may not otherwise be evident to a user. The insurance bundle may be presented to the user with dynamically generated scenarios that support the recommendation with data associated with the user. A technical benefit of this approach is that the user can readily understand the reasons why each of the policies of the bundle of insurance policies was recommended. Another technical benefit provided by the techniques described herein is that the machine learning models may be trained using data that has been parsed and standardized into a standard schema. Furthermore, the data to be analyzed by the machine learning models may also be parsed and standardized. As a result, the machine learning models are receiving data in a format that utilizes descriptions that are consistent with the training data used to train the models. Consequently, the predictions provided by the models may be significantly improved in comparison to models which are not trained using such a technique. The techniques provided herein also provide for substantially real-time analysis of information from a combination of data sources that may also significantly improve the predictions provided by the machine learning models and provide the user with recommendations that are more likely to provide for the user's needs. These and other technical benefits of the techniques disclosed herein will be evident from the discussion of the example implementations that follow. Furthermore, the techniques provided herein satisfy a long-felt need for improving the recommendations that may be made to users for selecting a bundle of insurance policies that covers the complex and variable needs of the users. Furthermore, the solution provided to this problem is rooted in computer technology to overcome a problem arising in realm of computer systems for providing substantially real-time analysis of demographics, risk, and need to provide the users with recommendations that fit their current needs.

FIG. 1 is a diagram showing an example computing environment 100 in which the techniques disclosed herein for insurance claims analysis and adjudication may be implemented. The computing environment 100 may include a claims analysis and adjudication system (CAAS) 105, one or more client devices 115, one or more insurer portals 125, one or more provider portals 135, and one or more third-party data providers 130. The example implementations shown in FIG. 1 includes three client devices 115a, 115b, and 115c, but the techniques described herein may be used with a different number of client devices 115. The client devices 115a, 115b, and 115c may communicate with the CAAS 105, the insurer portals 125, provider portals 135, and/or the third-party data providers via the network 120. The CAAS 105 may also communicate with the client devices 115a, 115b, and 115c, the insurer portals 125, the provider portals 135, and/or the third-party data providers 130 via the network 120. The network 120 may include one or more wired and/or wireless public networks, private networks, or a combination thereof. The network 120 may be implemented at least in part by the Internet.

The client devices 115a, 115b, and 115c may be used by an insured to access the services provided by the CAAS 105, insurance information from the insurer portals 125, and/or information from the third-party data providers 130. The client devices 115a, 115b, and 115c are each a computing device that may be implemented as a portable electronic device, such as a mobile phone, a tablet computer, a laptop computer, a portable digital assistant device, a portable game console, and/or other such devices. The client devices 115a, 115b, and 115c may also be implemented in computing devices having other form factors, such as a desktop computer, vehicle onboard computing system, a kiosk, a point-of-sale system, a video game console, and/or other types of computing devices. While the example implementation illustrated in FIG. 1 includes three client devices, other implementations may include a different number of client devices. The client devices 115a, 115b, and 115c may be used to access the applications and/or services provided by the insurer portals 125 and/or the CAAS 105.

The insurer portals 125 may be provided by insurance providers as a means for the insured user to access their policy information, make policy payments, obtain new policies, to submit claims on existing policies, and/or perform other actions related to the managing of the insured's insurance. An insured user may have policies with multiple insurers, and thus, may have to access multiple insurer portals 125 to obtain information related to each of their insurance policies. Consequently, the insured user must learn to navigate multiple insurance portals that may have significantly different layouts in order to access their policy information, submit claims and/or check on claim status, or perform other actions related to their policy.

The service provider portals 135 may provide a means for doctors, dentists, optometrists, and/or other medical professionals to submit claims to the insurers on behalf of an insured user. The service provider portals 135 may provide means for the providers to check on the status of a claim with an insurer. The service provider portals 135 may also permit the providers to amend and/or resubmit claims.

The CAAS 105 provides a cloud-based or network-based portal for accessing the services provided by the CAAS 105. The CAAS 105 may be configured to provide secure and delegated access to insurance claims for insured users. The CAAS 105 may implement a claims application programming interface (API) infrastructure that allows the insured users to access their insurance claims data and to provide various services such as claims analysis and adjudication services, guidance for optimizing prescription benefits, guidance for optimizing medical spending account (MSA) usage, guidance for proactive benefits engagement, services which may assist the insured in selecting a bundle of insurance products that satisfies the insured requirements, and/or other services related to optimizing the insurance coverage and utilization by the insured. Among the services provided by the CAAS 105, the CAAS 105 provides substantially real-time claims analysis and adjudication. The CAAS 105 may utilize a machine-learning model or models trained to analyze the claims to guide the user through submitting the claims to the appropriate insurer and to provide other advice for optimizing the use of the coverage provided to the user by their policies. The CAAS 105 may also respond to changes in the demographic data of the user and may provide a proposed bundle of insurance policies that meet the changing needs of the user. The example implementations which follow provide additional details describing these and other features of the CAAS 105.

The CAAS 105 may be configured to collect policy and claims information for users from the insurer portals 125, to analyze the information included in the policy information to obtain coverage information. The coverage information may include which types of claims are covered by each policy, the limits of coverage provided by each policy, other information that may be used to determine whether an insurer may cover a particular claim, or a combination thereof. The CAAS 105 may be configured to implement a set of secure and authenticated pipelines that are configured to allow members to link to their accounts with their insurance providers to obtain plan information, claims information, or both. The CAAS 105 may provide a user interface that provides a list of supported insurers. The user may select an insurer from the list of supported insurers and the user interface guides the user through setting up the connection with the user's account with that insurer. The user may securely provide authentication details that permit the CAAS 105 to securely access the policy information and/or claims information provided through the insurer portals 125. The CAAS 105 may access the policy information, claims information, or both, analyze this information, and convert the information to a unified and standardized schema for this information. The standardized information may be stored by the CAAS 105 to provide various services to the user, which will be discussed in greater detail with respect to the example implementation of the CAAS 105 shown in FIGS. 2 and 3.

The third-party data providers 130 are additional data sources that may be accessed by the CAAS 105 to obtain additional information for a user. The CAAS 105 may be configured to use the third-party data to supplement information collected from the user. The CAAS 105 may be configured to collect at least some demographic information from the user by presenting a set of dynamically generated questions to the user. The questions presented to the user may be dynamically selected based at least in part on the user's responses to previous questions, to information included in the third-party data, or a combination thereof. The third-party information and/or information that may be collected from the user may include, but is not limited to, the user's medical history, past insurance consumption, the user's financial profile (debts, assets, liabilities), credit history, family information, psychographics, interests, occupation, salary, physical activity, and other information that may be used by the CAAS 105 to facilitate providing insurance plan recommendations to the user. The CAAS 105 may query the third-party data providers 130 for information and may reformat the data into a standard schema used by the CAAS 105 for storing and analyzing the data. The CAAS 105 may also be configured to disambiguate the data received from the third-party data sources where the data includes information associated with multiple people who may or may not be the user. Additional details of data disambiguation are provided in the examples which follow.

Figure 5A:
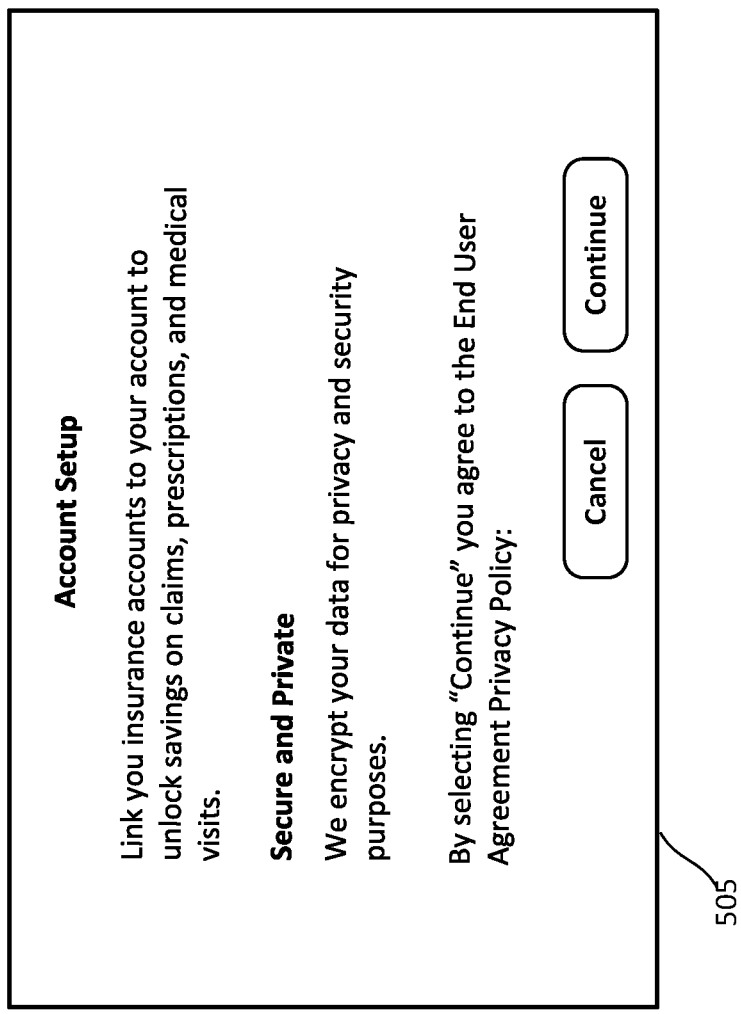
Figure 5C:
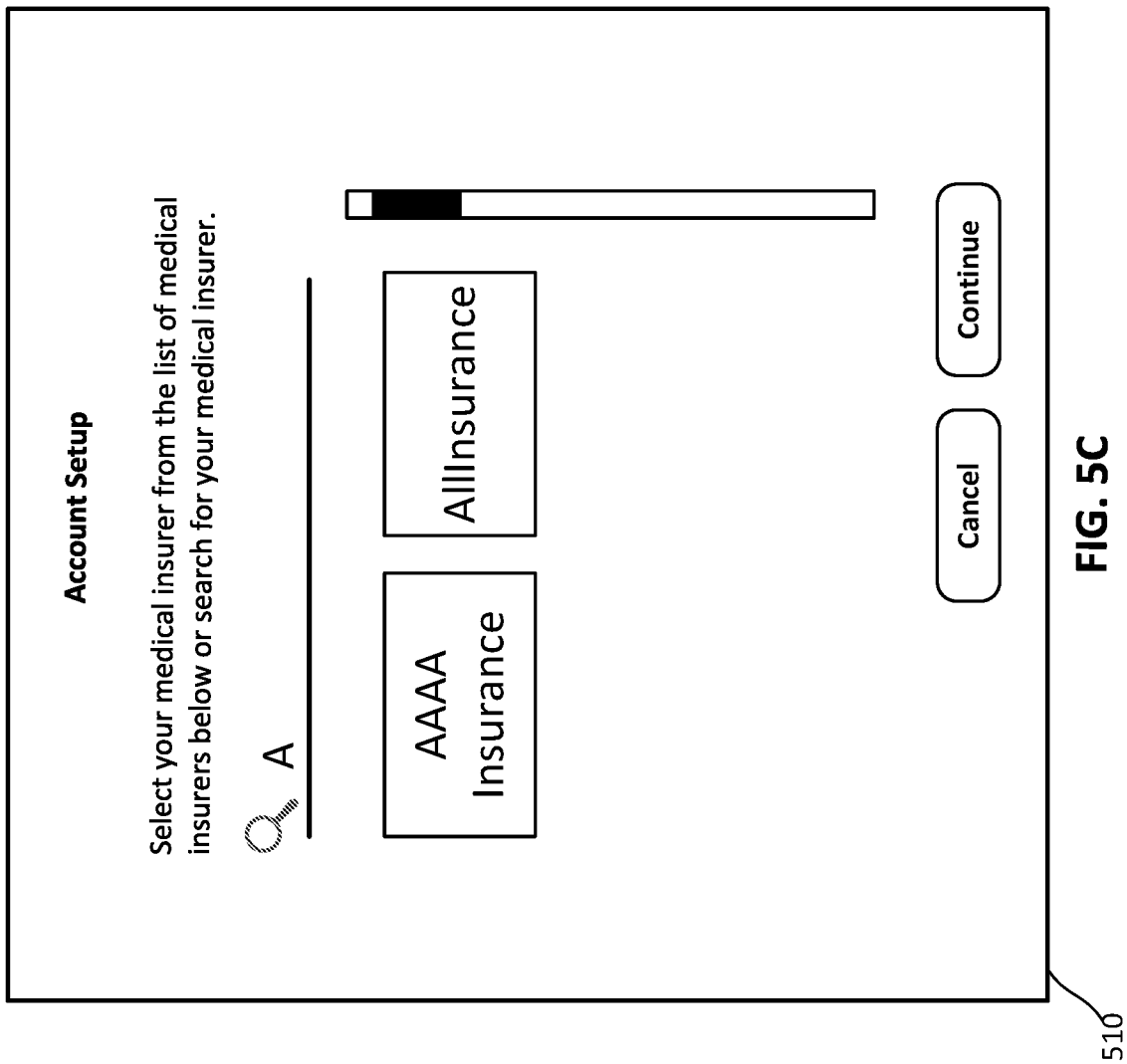
Figure 5D:
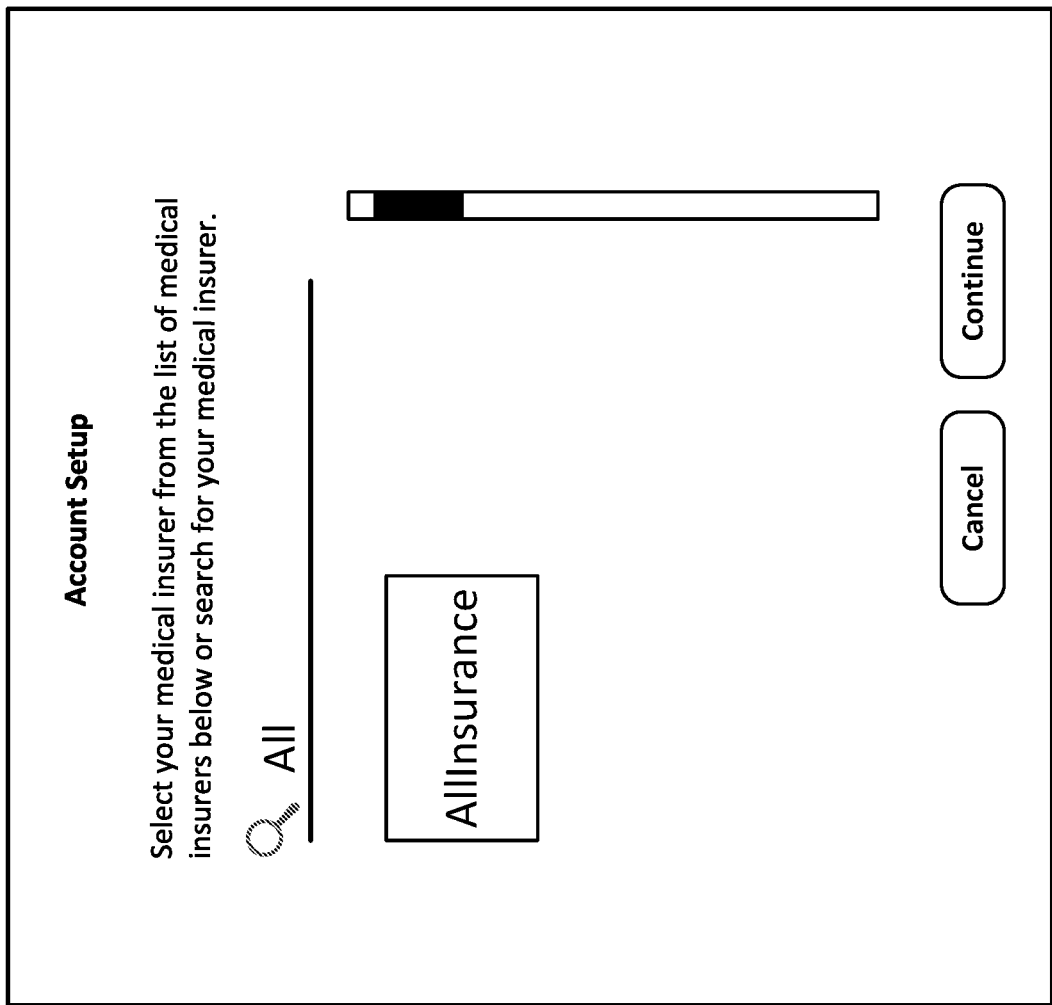
Figure 5E:
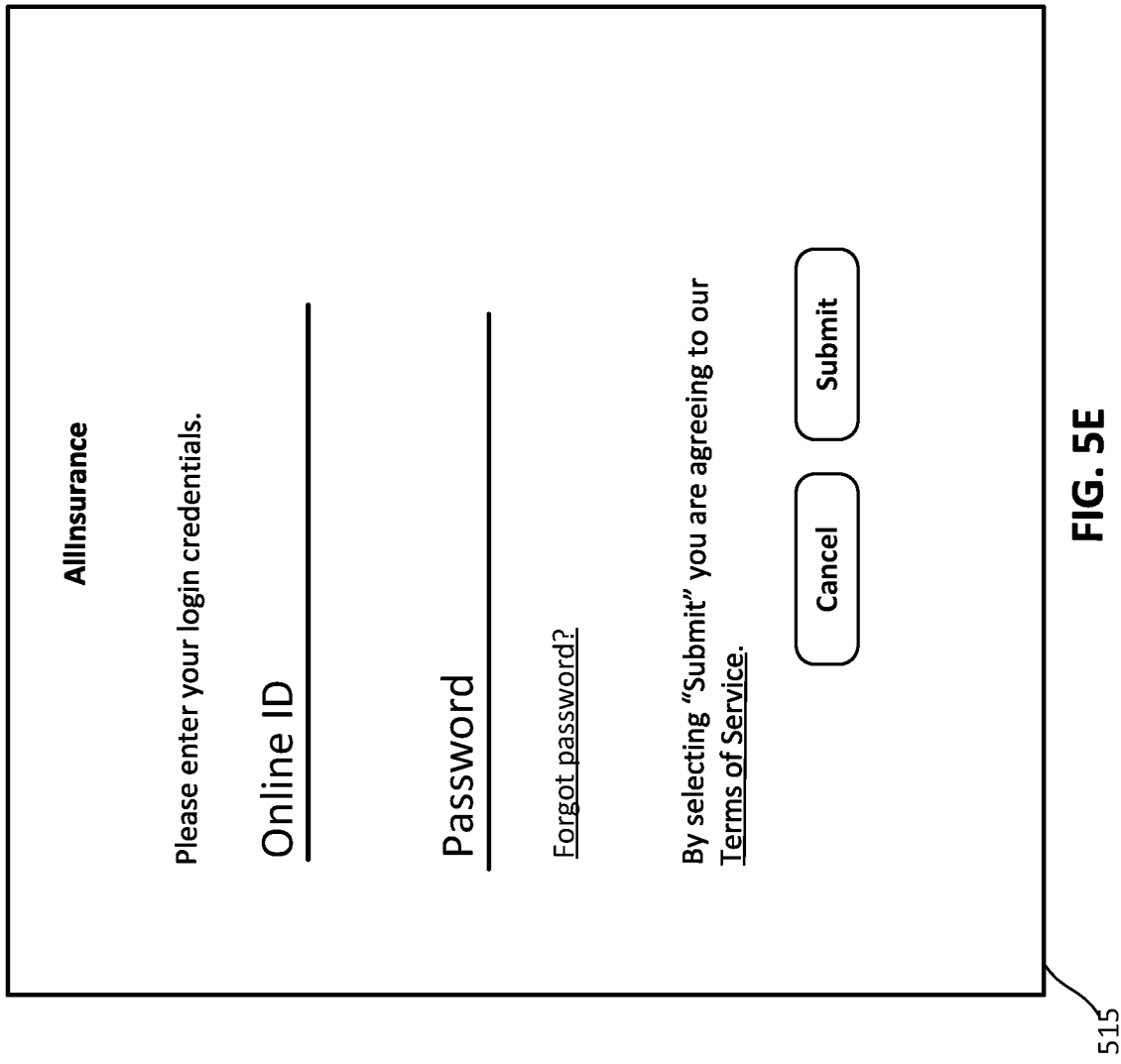

FIGS. 5A-5H show an example of the CAAS 105 guiding a user through the process of linking the user's account with an insurer to the user's CAAS account so that the CAAS 105 may obtain policy and claim information associated with the user from the insurer portal 125. FIG. 5A shows a user interface 505 for starting the setup process that presents information to the user regarding the account setup process. The user may click on the "Continue" button to cause the CAAS 105 to advance to the user interface 510 shown in FIG. 5B. The user interface 510 provides a list of insurers to which the CAAS 105 has been configured to permit the user to link the CAAS account to the user's account on the insurer's system. The user may select the icon associated with a particular insurer or type the name of the insurer in the search field. FIGS. 5C and 5D show that the list of insurers may be narrowed dynamically as the user types in the search field. FIG. 5E shows an example of a user interface 515 that may be displayed for the selected insurer. The user may provide their authentication credentials for the insurer portal and click submit. The CAAS 105 will attempt to access the insurer portal 125 using the provided authentication criteria. FIGS. 5F and 5G show an example two-factor authentication user interface 520 that may be used to further secure access to the user account on the insurer portal 125. Once the user has been authenticated with the insurer's portal, the user interface 525 may be displayed to confirm that the accounts have been linked. The CAAS 105 may then access claims information, policy information, and/or other information from the insurer portal 125.

Figure 2:
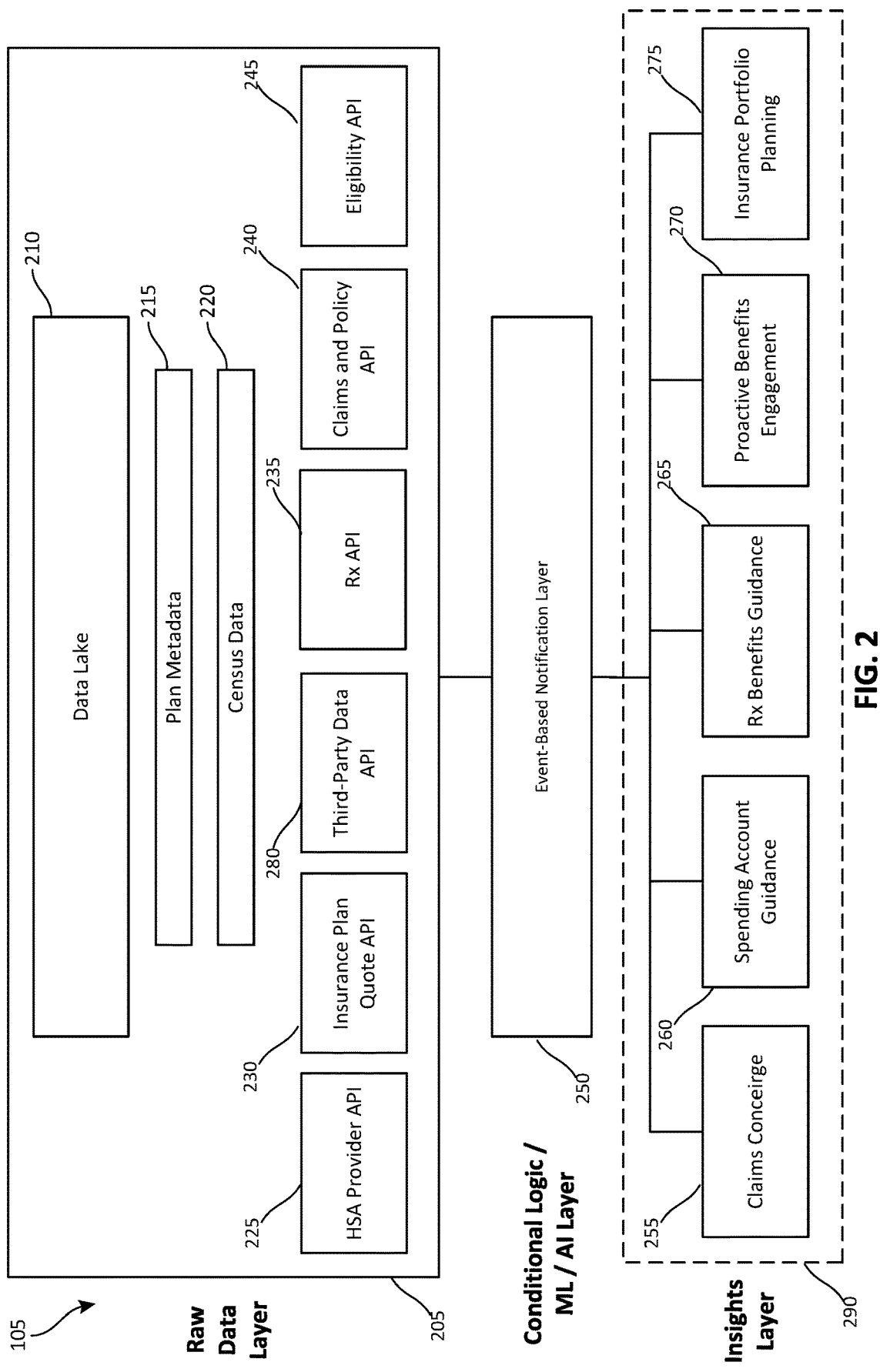
FIG. 2 is a diagram of an example architecture that may be used, at least in part, to implement the claims analysis and adjudication system (CAAS) shown in FIG. 1.

FIG. 2 is a diagram of an example implementation of a CAAS 105 shown in FIG. 1 that shows additional elements of the CAAS 105. The CAAS 105 shown in FIG. 2 includes three layers: (1) a raw data layer 205, (2) an event-based notification layer 250, and (3) an insights layer 290. The raw data layer 205 may be configured to obtain insurance data for users from various data sources, to convert this data to a unified and standardized schema, and to store the user data for analysis by the event-based notification layer 250 and/or the insights layer 290 to provide various insurance-related services to the users. Additional details of the functions of each of these layers will be described in greater detail in the examples which follow. In some implementations, the functions of each of these layers may be grouped together into a different number of functional layers. Furthermore, the functionality of each of the layers may be implemented on separate servers in some implementations, and the servers may be communicably coupled over public and/or private network connections to permit the various components of the CAAS 105 to exchange and analyze data.

The raw data layer 205 may include a data lake 210, a plan metadata data store 215, a census data datastore 220, a health savings account (HSA) provider API 225, an insurance plan quote API 230, a prescription API 235, a claims and policy API 240, an eligibility API 245, and a third-party data API 280. The APIs provide pipelines for obtaining data that that the CAAS 105 may use to provide various insurance-related services. User data may be protected by secure and authenticated pipelines when accessing sensitive data. The CAAS 105 may guide a user through setting up authentication with the external data sources to allow the CAAS 105 to securely access the user data.

Figure 3:
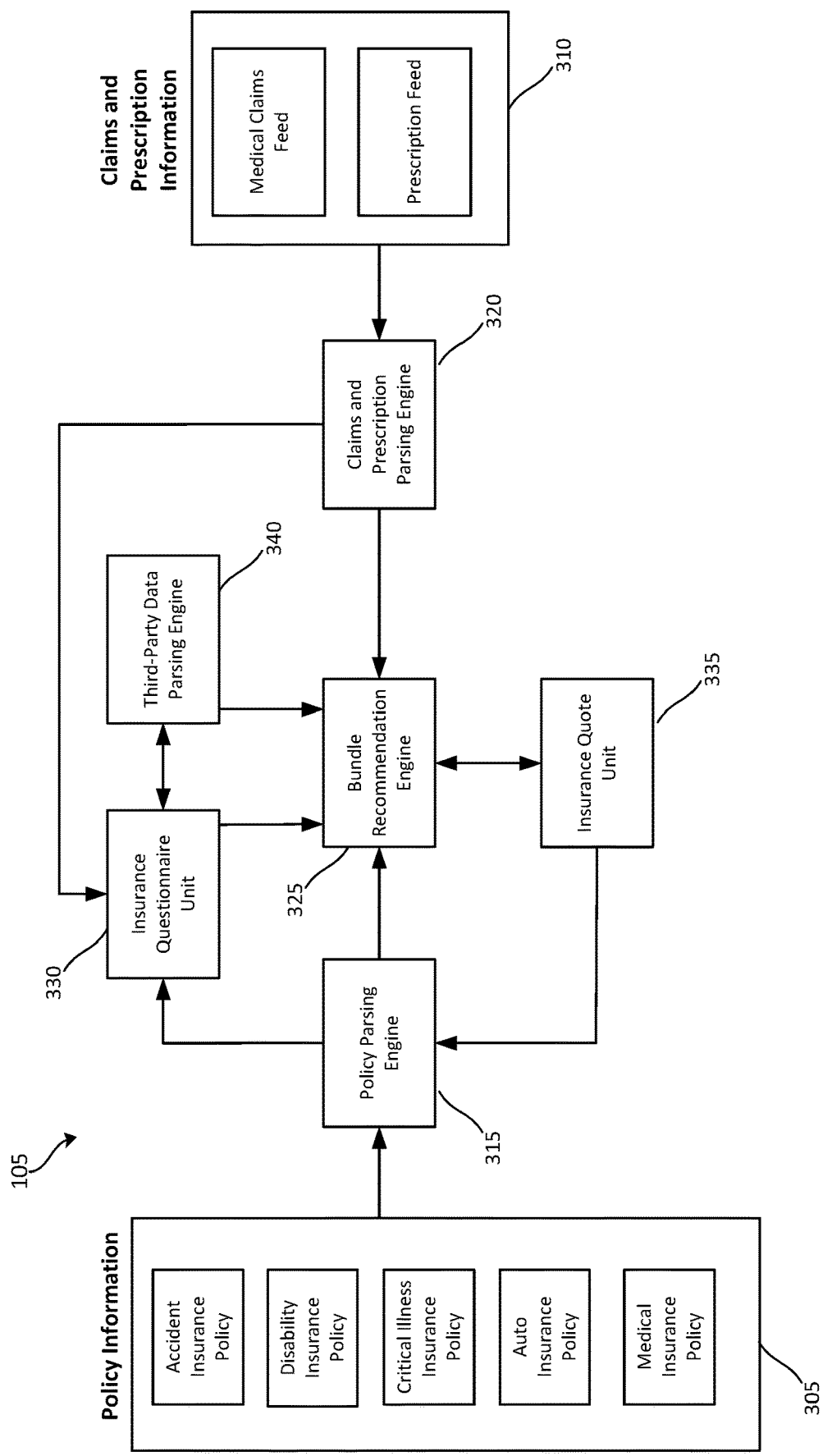
FIG. 3 is a diagram of an example architecture that shows additional details of a CAAS which may be used to implement the CAAS shown in FIGS. 1 and 2.

The data lake 210 may be used to store raw user data, raw claims data, and raw policy data that has been obtained from one or more external data sources, such as but not limited to the insurer portals 125 and the third-party data providers 130. Raw data, as used herein, refers to an original data format in which the data was obtained from the external data source. The format of the raw data may depend on the type of data and the external data source from which the data was obtained. The raw data may be retained in the data lake 210, and the raw data 205 may be processed into a standard schema by one or more parsing engines of the CAAS 105. The standard schema defines a set of logical data structures that may be used by the CAAS 105 storing and analyzing data. FIG. 3, which will be discussed in greater detail below, includes two parsing engines, a policy parsing engine 315 and a claims and prescription parsing engine 320 for parsing data. While the example shown in FIG. 3 includes two separate parsing engines, the functionality of the parsing engines may be combined into a single parsing engine or into more than the two parsing engines shown in FIG. 3. The standardized policy data may be stored in the plan metadata 215.

The policy data may include coverage information, including but not limited to the types of claims are covered by each policy, the limits of coverage provided by each policy, other information that may be used to determine whether an insurer may cover a particular claim for a user. The census data 220 may include demographic information that is collected from the user by the CAAS 105, information about the user obtained from third-party data providers 130, information obtained from the insurer portals 125, and/or other information about the users that may be used by the CAAS 105 to provide recommendations to the user regarding insurance-related issues. The user-related data obtained from these various sources may be formatted into a standard schema by one or more parsing engines of the CAAS 105 and stored in the census data 220.

The raw data layer 205 shown in FIG. 2 includes six API units configured to implement APIs for accessing data from various sources. Some implementations of the raw data layer 205 of the CAAS 105 may include a different number of APIs for accessing data from the various data sources. The types of data sources accessed and processed by the raw data layer may depend at least in part on the functionality provided by the insights layer 290 discussed in greater detail in the examples which follow.

The claims and policy API 240 is configured to obtain policy information and/or insurance claims information from insurers via the insurer portals 125. As discussed in the preceding examples, the CAAS 105 may be configured to provide a user interface that guides the user through linking their account with the CAAS 105 to their accounts with their insurers. The claims and policy API 240 may be configured to retrieve policy information and/or claims information from each insurer and store the raw data in the data lake 210. The insurance policy information may be converted to the standard schema by the policy parsing engine 315 and the claims information may be converted to a standard schema by the claims and prescriptions parsing engine 320 shown in FIG. 3.

The policy information for users may be kept up to date in substantially real-time. The claims and policy API 240 may be configured to periodically check for updates to the policy information for users. The claims and policy API 240 may also check for updates to the policy information for the user in response to a request from the event-based notification layer 250 or the insights layer 290. In some implementations, the claims and policy API 240 may receive updates to the claims information and/or the policy information from the insurer in response to the changes or renewal of a policy or in response to claims being submitted to the insurer for reimbursement.

The HSA provider API 225 may be configured to obtain information from one or more HSA providers. The HSA provider API 225 can obtain information associated with the HSA account of a user, such as but not limited to the current balance, historical reimbursement information for claims reimbursed by the HSA account, and/or other information associated with the usage of the HSA account. The HSA account information may be used by the CAAS 105 to build a historical model of the number and types of claims submitted for reimbursement by the user and to make predictions for recommended future funding of the HSA based on the historical usage. The HSA account information may also be considered by the CAAS 105 when analyzing the insurance coverage of the user and for recommending coverage that accommodates the needs of the user.

The prescription API 235 may be configured to obtain prescription price information from a pharmacy benefits manager (PBM). Information regarding the prescriptions that a user has been prescribed may be obtained directly from the user and/or determined based on the claims information obtained from the insurance providers via the claims and policy API 240. The prescription price information may be utilized by the prescription benefits guidance unit 265.

The insurance plan quote API 230 may be configured to obtain quotes for insurance coverage from insurers that may be used by the CAAS 105 to create a comprehensive bundle of insurance policies for a user based at least in part on predicted insurance consumption by the user. The insurance plan quote API 230 may be configured to submit requests for quotes to insurers for medical insurance, dental insurance, accident insurance, hospital indemnity insurance, auto insurance, and/or other types of insurance. The insurance portfolio planning unit 275 may use the quote information to build a comprehensive insurance plan for the user that is based on the needs of the user. The insurance portfolio planning unit 275 may determine the needs of the user based on user data that includes, but is not limited to, the user's medical history, past insurance consumption, the user's financial profile (debts, assets, liabilities), family information, psychographics, interests, occupation, salary, physical activity, and/or other information that may be used to infer the needs of the user.

The eligibility API 245 may be configured to verify enrollment of a user with an insurer. The API 245 may be used to determine whether the user is covered by a particular policy and whether the user is eligible for certain types of claims to be reimbursed by the insurer. The eligibility information may be utilized by the CAAS 105 to determine whether a particular claim or type of claims may be covered by a particular insurer. The eligibility information may be accessed substantially in real-time so that recommendations provided by the CAAS 105 are based on current enrollment status of the user.

The third-party data API 280 may be configured to submit queries for third-party data to the third-party data provider 130. The third-party data sources may include but are not limited to sources of medical history data, financial profile information, credit history information, marital status information and/or family information, occupation, salary, and/or other information that may be used by the CAAS 105 to provide various recommendations to the user. The third-party data API 280 may be used by the various components of the CAAS 105 to query the various data sources for third party data.

The event-based notification layer 250 may utilize conditional logic, machine learning models, and/or artificial intelligence systems for analyzing the data obtained and/or generated by the raw data layer 205. The event-based notification layer 250 may be configured to analyze the data from the raw data layer 205 to support the functionality of the services provided by the insights layer 290. The event-based notification layer 250 may utilize one or more machine learning models to analyze the data maintained by the raw data layer 205. The event-based notification layer 250 may implement elements of the bundle recommendation engine 325 shown in FIGS. 3 and 4.

The insights layer 290 may provide various services to the user based on the analysis of the data by the event-based notification layer 250. The insights layer 290 includes a claims concierge unit 255, a spending account guidance unit 260, a prescription benefits guidance unit 265, a proactive benefits engagement 270, and an insurance portfolio planning unit 275.

The claims concierge unit 255 may be configured to analyze claims data and to provide recommendations to the user for submitting the claims to an insurer. The claims concierge unit 255 may be configured to automatically analyze claims data to identify claims that may be paid by an insurer. The claims concierge unit 255 may also provide recommendations in response to a request from a user to analyze one or more pending insurance claims. Additional features of the claims concierge unit 255 are shown in the examples which follow.

The spending account guidance unit 260 may provide guidance to the user for optimizing the funding of the MSA based on prior health plan consumption and utilizing the MSA funds to reimburse medical claims costs. The prescription benefits guidance unit 265 may provide guidance to the user for providing prescription price guidance to the user including prices at which prescription medications are being offered at pharmacies located near the user.

The proactive benefits engagement unit 270 may provide recommendations for the user for optimizing the usage of their benefits. The proactive benefits engagement unit 270 may be configured to provide meaningful and actionable notifications to encourage users to engage with the benefits provided by their insurance policies. The proactive benefits engagement unit 270 may consider the personal finances of the user when making recommendations to the user regarding the usage of the user's benefits.

The insurance portfolio planning unit 275 may provide recommendations to the user for building insurance bundles that consider the user's demographics, risk aversion of the user, and the needs of the user. Additional details of the insurance portfolio planning unit 275 are shown in FIGS. 3, 4, 6A-6G, and 7.

FIG. 3 is a diagram that shows an example implementation of a bundle recommendation engine 325 that may be implemented by the CAAS 105. The bundle recommendation engine 325 may be configured to provide machine-learning driven recommendations for comprehensive insurance plans based on the individual demographics of a user, the risk aversiveness of the user, and the coverage needs of the user. The bundle recommendation engine 325 may be implemented in part by the raw data layer 205, the event-based notification layer 250, and the insights layer 290.

The policy information 305 may include multiple insurance policies, such as but not limited to medical insurance policies, dental insurance policies, accident insurance policies, disability insurance policies, critical illness insurance policies, auto insurance policies, and/or other types of insurance policies. The bundle recommendation engine 325 may use this information to obtain information about the current insurance coverage of a user and to obtain information for claims that were previously made against the user's insurance policies. The past claim information may be used by the bundle recommendation engine 325 to predict future claims consumption by the user based upon a demographic cluster into which the user is predicted to fall. The predicted consumption information may be used to generate a recommended comprehensive insurance plan for the user that includes a bundle of insurance policies.

The policy information 305 may be obtained by the claims and policy API 240 of the raw data layer 205 shown in FIG. 2. Electronic copies of the policies may be obtained from the insurers in a Portable Document Format (PDF), or another electronic format supported by each insurer. Insurers may support different electronic file formats and the layout of the policy information provided by each insurer may vary. The policy information obtained from the insurers may be stored in the data lake 210 of the raw data layer 205. The policy parsing engine 315 may be configured to analyze the raw policy data obtained from the insurers and to convert the policy information to a standard schema. The standardized information may be stored in the plan metadata 215. The plan metadata may include coverage information, policy limits, deductible information, claims information, and/or other information that may be used by the CAAS 105 to determine whether a particular insurer may reimburse the policy holder for a particular type of claim or claims. The policy information may also be used by the bundle recommendation engine 325 to provide guidance to the user regarding the user's current insurance coverage versus coverage provided by a recommended plan.

The policy parsing engine 315 may be configured to use fuzzy matching techniques to map policy coverage information extracted from the insurance policies to standardized coverage information. Insurers may use slightly different language to describe the coverage provided. The policy parsing engine 315 may be configured to map the policy coverage information with a set of standardized insurance coverage descriptions maintained by the CAAS 105. The standardized insurance coverage descriptions may include descriptions of types of coverage that may be offered by insurers. The policy parsing engine 315 may be configured to perform a probabilistic data match on the coverage information provided in an insurance policy with the standardized coverages descriptions. The policy parsing engine 315 may be configured to select a standardized description that is associated with the highest probability of being a match with the policy coverage description. The matching standardized description may be stored in with the policy information in the plan metadata 215 and may be used by the bundle recommendation engine 325 to determine whether the user has a policy that is likely to cover the claim.

The policy parsing engine 315 may also be configured to receive plan quote information from the insurance quote unit 335. The insurance quote unit 335 may be configured to obtain insurance policy quotes from insurers via the insurance plan quote API 230. The insurance plan quote API 230 may be configured to request policy information and quotes for purchasing the coverage from insurers via the insurer portals 125 in response to queries from one or more elements of the CAAS 105. For example, the bundle recommendation engine 325 may be configured to request policy information for one or more types of insurance policy that may be included in a bundle of policies to be recommended to the user. The policy parsing engine 315 may parse the policy information in a similar manner as discussed above to standardize the policy information received with the quotes. The raw policy data may be stored in the data lake 210 and the standardized policy information may be stored in the plan metadata 215. The information associated with the quotes may be stored and used to generate an insurance plan recommendation for the user. The information associated with a quote may be discarded after a threshold period of time has passed, because the availability of the insurance plans and the quoted prices may change over time.

Mapping the policy coverage information to standard descriptions may provide a significant technical benefit by improving the predictions that are provided by the machine learning models used by the bundle recommendation engine 325. The machine learning models may be trained using training data that includes the same standard insurance coverage descriptions that will be used by the bundle recommendation engine 325 to determine whether a particular claim is likely to be covered by a user's insurance policy. Thus, the machine learning models may be presented with policy coverage data for analysis that utilizes descriptions consistent with the coverage descriptions included in the training data used to train the model.

The claims and prescription information 310 may include substantially real-time information from a medical claims feed and prescription feed. The medical claims information represents insurance claims that the user has submitted or has had submitted on their behalf for reimbursement. The prescription information represents prescriptions that have been prescribed to the user and may be submitted for reimbursement to an insurer. The claims and/or prescription information may be obtained by the claims and policy API 240 shown in FIG. 2 and the data stored in the data lake 210. The claims and prescription information obtained from each of the insurers may be in different electronic formats and/or layouts. The claims and prescription information may be processed by the claims and parsing engine 320 to convert the claims and prescription information into the standard schema utilized by the CAAS 105. The claims and prescription information in the standardized schema may be stored with the plan metadata 215.

The claims and prescription parsing engine 320 may be configured to use fuzzy matching techniques to map the claims and prescription information 310 to standardized claims and prescription descriptions before the claims and prescription information is analyzed by the bundle recommendation engine 325. Medical providers may use inconsistent language to describe the procedures performed. One medical provider may describe the same procedure in a slightly different way than another provider. Such inconsistencies in the description of the procedures performed can make determining whether a particular policy covers a particular claim or prescription. The set of standardized claim and prescription descriptions may provide a consistent set of descriptions that may be associated with claims and prescriptions. The claims and prescription parsing engine 320 may be configured to perform a probabilistic data match on the claims and prescription information 310 with the standardized claim and prescription descriptions. The claims and prescription parsing engine 320 may be configured to select a standardized description that is associated with the highest probability of being a match with the description of the procedure performed and/or other information included in the claim and/or prescriptions submitted to the insurer on behalf of a user.

The standardized description matched with a claim may be stored with the claim information in the plan metadata 215 associated with the claim. The standardized description may also be used by the bundle recommendation engine 325 to determine whether the user has a policy that is likely to cover the claim. Mapping the claims and prescription information to standard descriptions provides the technical benefit of improving the predictions that are provided by the machine learning models used by the bundle recommendation engine 325. The machine learning models may be trained using training data that includes the same standard claim and/or prescription descriptions that will be used by the bundle recommendation engine 325 to recommend an insurance plan to the user. Thus, the machine learning models are presented claims and prescription descriptions for analysis that utilizes descriptions consistent with the claims and prescription descriptions included in the training data used to train the models.

If the probability of the standardized description matching a particular claim is less than a predetermined threshold, the claims and prescription parsing engine 320 may flag the claim for additional processing. The user may be prompted to provide additional information that may be used to help disambiguate the claim and/or to request that a different description for the claim be provided. Standardizing the descriptions of the claims may increase the likelihood that the bundle recommendation engine 325 may correctly determine prior insurance consumption and recommend an appropriate insurance plan to the user.

The third-party data parsing engine 340 may be configured to obtain data from the third-party data providers 130 and to parse the third-party data. The third-party data may include but is not limited to credit history information, debt information such as mortgage, automobile, or student loans, rental history for renters, cost of living information related to a geographical area in which the user is living, and/or other information that may assist the bundle recommendation engine 325 to develop a comprehensive insurance plan for the user. The third-party data parsing engine 340 may convert the raw data received from the third-party data providers 130 to the standard schema used by the CAAS 105. The third-party data parsing engine 340 may also be configured to identify ambiguous data received from the third-party data source 130 and to attempt to disambiguate the ambiguous data. The data received from the third-party sources may not be definitively associated with the user for whom the data is associated, and the third-party data parsing engine 340 may then analyze the data in an attempt to determine which, if any, of the data obtained is actually associated with the user. For example, the third-party data associated queries for a user may include loan information, but the query returns loan data for three people with similar names as the user. The third-party data parsing engine 340 may need to disambiguate the information obtained. The third-party data parsing engine 340 may use fuzzy matching techniques to attempt to match the loan data with third-party data and/or data obtained from the user known to be associated with the user. The third-party data parsing engine 340 may obtain information from the user via the dynamic questions presented by the insurance questionnaire unit 330 described below. For example, with respect to the loan information, a dynamic question or set of questions may be presented to the user to determine whether any of the loan information is actually associated with the user. Information that is found to not be associated with the user may be discarded. The fuzzy matching techniques may produce a correspondence value representing how closely the ambiguous data matches with the known data associated with the user. The insurance questionnaire unit 330 may be configured to discard a portion of the ambiguous data that has a correspondence value that is less than a threshold value as being unrelated to the user.

The insurance questionnaire unit 330 may be configured to present a set of dynamically generated questions to the user to collect information from the user that may be used by the bundle recommendation engine 325 to recommend a bundle of insurance policies that satisfies the needs of the user. The dynamically generated questions may be used to collect information such as but not limited to the user's medical history, past insurance consumption, financial profile information (debts, assets, liabilities), credit history, family information, psychographics, interests, occupation, salary, physical activity, and other information that may be used by the bundle recommendation engine 325 to determine the needs of the user and to present insurance plans that satisfy those needs. The insurance questionnaire unit 330 may also consider the standardized policy information, claims information, and prescription information provided by the policy parsing engine 315 and the claims and prescription parsing engine 320 when determining which information to request from the user. Past medical claim information may be used by the bundle recommendation engine 325 to identify medical conditions that user or an insured family member has experienced. Chronic medical conditions which may require ongoing treatment may be identified and insurance plans which provide coverage for these conditions may be recommended. Chronic medical conditions such as heart disease, cancer, chronic lung disease, kidney disease, Alzheimer's disease and/or dementia-related chronic conditions, and/or other medical conditions requiring long-term medical intervention and/or long-care may be identified.

The insurance questionnaire unit 330 may obtain third-party data from the third-party data parsing engine 340 which may be used to generate further questions that may be presented to the user. The questions may be used to disambiguate the information that was provided by the user and/or obtained from the third-party data sources. The insurance questionnaire unit 330 may be configured to generate questions to obtain information from the user that may be used to learn about the user's risk exposure. The CAAS 105 can use this information and the user's demographic information to provide a recommended bundle of insurance policies that cover these risks in a manner that is tailored to the specific needs of the user. Furthermore, the user's response to a question may trigger the insurance questionnaire unit 330 to query for additional third-party data which may be processed by the third-party data parsing engine 340. The dynamically generated questions may be used to further clarify information obtained from the user and/or from third-party data sources. For example, if the third-party information indicates that the user has a mortgage, automobile loan, student loan debt, and/or other types of debt, the insurance questionnaire unit 330 may be configured to present follow-up questions to the user to determine how the user may deal with this debt in certain situations. For example, the insurance questionnaire unit 330 may be configured to present questions regarding how long the user may be able to continue paying the debt in the event of a loss of income and how confident the user is regarding their continued ability to pay the debt. These and other types of questions may be used to infer financial resources of the user, such as available cash resources, that the user may utilize to cover expenses in the event of an emergency. The bundle recommendation engine 325 may use this information to recommend policies that consider the financial situation of the user to provide policies that may cover loss of income. For example, if the user or an insured family member is a business owner, then business interruption insurance may be recommended to cover loss of income due to a peril covered by the insurance policy. The bundle recommendation engine 325 may also recommend a supplemental disability insurance policy for loss of income due to the insured or a family member becoming unable to work due to a medical condition or injury.

The insurance questionnaire unit 330 may implement one or more predictive machine learning models that may be used to identify additional formation that may be useful for the bundle recommendation engine 325 to make recommendations to the user. The predictive models may analyze the available demographic information provided by the user and/or collected from the one or more third-party data providers 130 to identify information that may be useful for further understanding the coverage needs of the user. The insurance questionnaire unit 330 may analyze the predictions to determine whether the user-data information and/or the third-party data included the information predicted to be useful. The insurance questionnaire unit 330 may identify gaps in the user-provided and/or third-party information. The insurance questionnaire unit 330 may attempt to obtain information to address the gaps in the information by querying the third-party data source 130 and/or may present dynamically generated questions to the user to obtain the information that may help fill the gaps in the information already obtained from the user and/or from the third-party data sources. The predictive models may be machine learning models trained to recognize relationships between types of data that may be relevant for recommending a comprehensive plan of policies to the user. Other type of prediction models and/or algorithms may also be used to implement the insurance questionnaire unit 330.

FIGS. 6A-6G, described in detail below, provide an example of a user interface that may be provided to the CAAS 105. These examples illustrate a series of questions that may be generated by the insurance questionnaire unit 330. The insurance questionnaire unit 330 may be configured to trigger the presentation of certain questions in response to the presence of or the absence of certain information in the data available to the insurance questionnaire unit 330.

The bundle recommendation engine 325 analyzes the information received from the policy parsing engine 315, the claims and prescription parsing engine 320, the insurance questionnaire unit 330, the insurance quote unit 335, and one or more third-party data providers 130 to generate a recommended bundle of insurance plans for the user. Additional implementation details of the bundle recommendation engine 325 are shown in FIG. 4.

Figure 4:
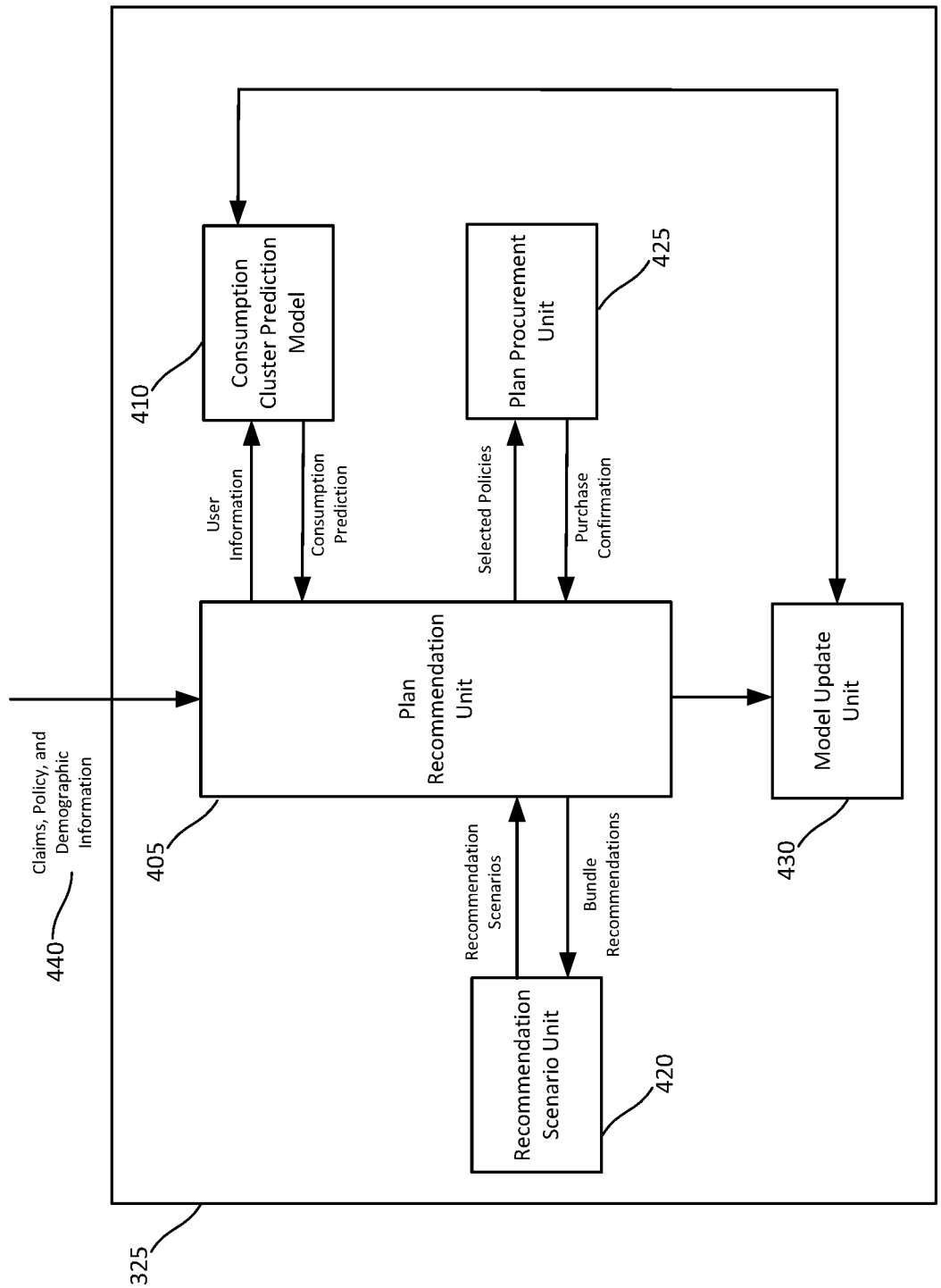
FIG. 4 is a diagram of an example architecture that shows additional details of the CAAS that may be used to implement the CAAS shown in FIGS. 1-3.

FIG. 4 is a diagram showing an example implementation of the bundle recommendation engine 325 of the CAAS 105. The bundle recommendation engine 325 may include a plan recommendation unit 405, a consumption cluster machine learning model 410, a dynamic scenario unit 420, a plan procurement unit 425, and a model update unit 430.

The bundle recommendation engine 325 may analyze user data from the various sources discussed above in order to recommend a comprehensive insurance plan that may include a combination of insurance policies, health savings accounts, supplemental insurance policies, and/or other insurance products that may be included as part of a comprehensive insurance plan. A recommendation may be generated on demand in response to a request from the user or automatically by the CAAS 105 in response to various events that indicate that the risk exposure of the user. Changes in the user's demographic information may trigger the CAAS 105 to generate a new recommended bundle of insurance to the user. The demographic information may be updated by the user and/or obtained from one or more third party data sources. For example, the plan recommendation engine may be configured to respond to a change in marital status, the birth or adoption of a child, the purchase of a new home, a job change, and/or other events for which a new insurance plan may be desirable to ensure that the user has adequate insurance coverage to reflect their changing needs. The bundle recommendation engine 325 may also be configured to guide the user through obtaining the recommended coverage from one or more insurers in response to the user indicating that they would like to obtain the coverage recommended by the bundle recommendation engine 325.

The plan recommendation unit 405 may be configured to obtain claims, policy, and user demographic information 440 to be analyzed to suggest a comprehensive insurance plan for the user. The claims, policy, and demographic information 440 include the standardized policy coverage information output by the policy parsing engine 315. The claims and policy information 440 may also include the claims and prescription information into the standard schema output by the claims and parsing engine 320. The claims, policy, and demographic information 440 also may include user demographic information, which may have been obtained by the insurance questionnaire unit 330.

The plan recommendation unit 405 may first analyze the claims, policy, and demographic information 440 to generate a claim cluster predication. The plan recommendation unit 405 may provide the information associated with the user to the consumption cluster prediction model 410. The consumption cluster prediction model 410 may be trained with demographic information, claims information, medical history information, financial profile information, credit history information, family information, psychographics, interests, occupation, salary, physical activity, and other information that may be used to group users into clusters of people having similar characteristics. The consumption cluster prediction model 410 may be configured to output a prediction that the user falls within a particular cluster associated with an anticipated medical spending over a predetermined period of time. The predetermined period of time may be a year in many implementations because many insurance policies renew annually. However, the period of time associated with the prediction may be different in some implementations.

The predicted medical spending for a cluster may include an amount spent and types of claims typically filed. The predicted medical spending may then be used to create a comprehensive insurance plan for the user that includes a recommended bundle of insurance policies based on the predicted medical spending. The comprehensive plan may include a bundle of insurance policies, health savings accounts, supplemental insurance policies, and/or other insurance products that may be included as part of a comprehensive insurance plan. The prediction accounts for numerous factors that may influence the risk exposure of the user and provides a recommended insurance bundle that may best match the needs of the user. The model considers a complex set of variables when making a recommendation that would be impractical, if not impossible, for a user to consider without such assistance. Thus, a technical benefit of this approach is that the machine learning models may recognize patterns in the insurance consumption and demographic information of the user to recommend a comprehensive insurance plan that may not otherwise be evident to a user.

The prediction model 410 may be trained initially with hand-labeled training data, but the model may be refined based on feedback on the predictions from the model update unit 430 discussed below. The consumption cluster prediction model 410 may be implemented using various types of machine learning models for which the training of the model may be refined.

The plan recommendation unit 405 may be configured to analyze the predicted medical spending for the user and to recommend a bundle of insurance policies, health savings accounts, supplemental insurance policies, and/or other insurance products that may cover the predicted medical spending. For example, if the predicted medical spending includes hospitalization resulting from an accident, the recommended bundle of insurance policies may include at least one insurance policy that covers hospitalization such as an accident insurance policy. The comprehensive plan may then be customized by the plan recommendation unit 405 to meet the needs of the user.

The plan recommendation unit 405 may customize the recommendation bundle of policies based on the user demographics data. The plan recommendation unit 405 may customize the recommend bundle of insurance policies based on the user's medical history, past insurance consumption, financial profile information (debts, assets, liabilities), credit history, family information, psychographics, interests, occupation, salary, physical activity, and other information to customize the recommended plan according to the needs of the user. The plan recommendation unit 405 may use this information to identify potential gaps between the coverage provided by the recommended bundle of policies and the needs of the user.

The following examples show how the plan recommendation unit 405 may identify such gaps in coverage and customize the recommend bundle of insurance policies to close these gaps. The plan recommendation unit 405 may take into account the marital status and/or the number of dependents of the user when customizing the plan. For example, the amount of life insurance recommended for the user may be increased based on if the user is married and for a user having a greater number of dependents. Furthermore, the plan recommendation unit 405 may recommend a Health Maintenance Organization (HMO) rather than a Preferred Provider Organization (PPO) for a user having a greater number of dependents to reduce out of pocket spending associated with the PPO. The plan recommendation unit 405 may also take into account previous medical spending by the user when customizing the recommended bundle of policies to the user. For example, if the user has a history of medical visits to an otolaryngologist for ear-related problems over the past several years, the plan recommendation unit 405 may select a comprehensive plan that covers all or most of the costs associated with such visits. The plan recommendation unit 405 may also consider the occupation of the user when making a recommendation because the risk of certain types of injuries and/or death may be greater for certain occupations. Furthermore, the income of the user and/or the user's spouse may be considered when making recommendations to ensure that the costs of the recommended policies do not exceed a threshold portion of the available income. The plan recommendation unit 405 may reduce the cost of the recommended bundle of policies by eliminating some types of coverage that may otherwise be recommended, by selecting less expensive plans, and/or reducing the policy benefits of one or more of the policies. In another example, the bundle associated with the prediction may recommend a health savings account (HSA), but the user may be provided with an employer-paid low deductible or no-deductible plan and the inclusion of the HSA may be unnecessary. In yet another example, the plan recommendation unit 405 may recommend a supplemental life insurance policy that was not included in the original recommended bundle of policies where the coverage of a life insurance policy provided by the user's employer is less than would be required to pay off the user's mortgage and to replace the user's income for a specified period of time. The supplemental life insurance policy may be recommended to cover the gap between the employer-provided life insurance policy and the desired amount of coverage. The customization provided by the plan recommendation unit 405 is not limited to these examples. The plan recommendation unit 405 may take into account other factors in addition to or instead of those discussed above when customizing the recommendation for a user.

The dynamic scenario unit 420 is configured to generate an insurance recommendation report based on the bundle of policies recommended by the plan recommendation unit 405. The CAAS 105 may cause the insurance recommendation report to be displayed on the client device 115 of the user. The insurance recommendation report provides detailed information on the comprehensive insurance plan that is being recommended to the user.

An example insurance recommendation report is shown in FIG. 6G and FIG. 10. The insurance recommendation report provides a list of the insurance policies that the plan recommendation unit 405 recommends. The insurance recommendation report may include an insurance provider from which the policy may be obtained, the cost of the policy, policy coverage information, and/or other information associated with the policy. The insurance recommendation report may also include a dynamic scenario associated with each policy that was recommended. The dynamic scenario provides a narrative that explains why the policy has been recommended to the user. The costs and/or savings associated with each policy may be described as well as other information that indicates why a particular policy has been recommended to the user. For example, a health spending account may be recommended to the user in combination with a high deductible insurance policy. The user may be predicted to file a minimal number of health claims during the year. Therefore, a higher deductible medical plan that is less expensive, but protects the user from catastrophic losses may be recommended. The user may also fund the HSA with tax-deductible money that may be used to offset medical costs during the year. These example scenarios show the type of information that may be provided in the plan recommendation report so that the user understands why the recommendation was made. The contents of the report are not limited to these specific examples.

The plan procurement unit 425 may be configured to enable the user to purchase policies included in the bundle of policies recommended to the user. Some of the policies may have already been issued to the user and will not need to be purchased by the user. For example, the user may have an existing employer-provided medical insurance policy which has already been provided to the user by the user's employer. Furthermore, some of the policies may not be available for purchase online. The plan procurement unit 425 may be configured to present instructions on a user interface of the CAAS 105. The plan procurement unit 425 may also provide the ability for the user to fill out the form electronically and print the form to be sent to the insurer via postal mail service. The plan procurement unit 425 may be configured to assist the user with obtaining forms to modify existing insurance policies if necessary. For example, if the recommendation includes changing enrollment from a Preferred Provider Organization (PPO) to a Health Maintenance Organization (HMO) for employer-provided insurance, the plan procurement unit 425 may be configured to obtain a copy of the forms necessary to make the change. The plan procurement unit 425 may also advise the user of any restrictions on making such a change, such as a change in family status or the change must be made during a specified open enrollment period. The plan procurement unit 425 may receive a summary of the actions taken to obtain the recommended policies.

The model update unit 430 may be configured to provide feedback to the consumption cluster prediction model 410 to refine the training of the model. The model update unit 430 may receive feedback directly from the user and/or from the plan recommendation unit 405. Feedback from the user may be obtained from the plan recommendation unit 405 in response to the user opting to not select one or more policies associated with a recommendation or completely rejecting the proposed bundle of policies. The feedback may be used to further refine the clustering predicted by the consumption cluster prediction model 410.

FIGS. 6A-6G are diagrams showing an example user interfaces of the CAAS 105 for collecting information for generating an insurance bundle recommendation and for presenting the insurance bundle recommendation. The user interfaces shown in FIGS. 6A-6G may be rendered by a browser application or a native application installed on a client device, such as the client devices 115a-115c shown in FIG. 1. The CAAS 105 may be configured to provide content renderable by a web browser installed on the client device. The CAAS 105 may also be configured to provide content to a native application installed on the client device which is configured to render the content received from the CAAS 105, to allow a user to interact with the content, and to receive requests for data and/or to perform various operations on the data maintained by the CAAS 105.

FIG. 6A is a diagram of an insurance dashboard user interface 605. The insurance dashboard user interface 605 may be implemented by the claims concierge unit 255 of the insights layer 290 of the CAAS 105. The insurance dashboard user interface 605 includes a notification pane 625, a claims details pane 630, and a claims analytics pane 635. The example implementation of the insurance dashboard user interface 605 shown in FIG. 6A shows one possible implementation of such an interface. Other implementations may present additional information to the user instead of or in addition to the information provided in this example.

The claims details pane 630 provides details of claims that were recently submitted to one or more insurers on behalf of the insured. The claims details may indicate who was covered, such as a member of the family of the insured user, when a particular service was performed, what service was performed, copay information, insurer information for the insurer to which the claim was filed, and/or other information related to the claims made to the insurer's policy. The claims information may be obtained from the plan metadata 215, the data lake 210, and/or another persistent data storage area of the raw data layer 205 of the CAAS 105. The claims details pane 630 may be configured to enable the user to obtain additional information for a claim by clicking on a link or other user interface component that may be clicked or otherwise activated by the user.

The claims analytics pane 635 may present information reporting various aspects of the user's insurance plan usage. The analytics may include information for multiple policy types, copays, and other out-of-pocket spending by the user, and/or other information related to the user's usage of their insurance policies. The claims analytics pane 635 may be configured to enable the user to obtain additional information of various elements of the analytics data by clicking on a link or other user interface component that may be clicked or otherwise activated by the user.

The notification pane 625 may be used to present informational messages to a user regarding their account information, policy information, claims information, or a combination thereof. The notification pane 625 may also include a link, button, or other means for activating functionality associated with the content presented in the notification pane 625. In the implementation shown in FIG. 6A, the notification pane 625 shows a message that indicates that the user may be able to submit a claim to her insurance company.

FIG. 6B shows a user interface 610 that may be displayed in response to the user clicking on or otherwise activating the link, button, or other means for activating functionality associated with the content presented in the notification pane 625. The user interface 605 may be created by the bundle recommendation engine 325. The user interface 610 shows the start of an example insurance planning questionnaire. The user interface 610 shows a first dynamically generated question of the questionnaire. The questions may be generated to collect information from the user that the bundle recommendation engine 325 may analyze to provide an insurance plan recommendation. The user may click the "Next" button to indicate to the CAAS 105 that the user would like to advance to the next question in the questionnaire shown in FIG. 6C.

FIG. 6C shows a next question in the questionnaire on the user interface 610. The questions shown in FIG. 6C has been selected based on the user's response to the question shown in FIG. 6B. In FIG. 6B, the user indicated that they participate in sports, and in FIG. 6C asks the user whether the user participants in any of a list of sports that may be considered "extreme" sports. The questionnaire included these questions because the participation in such sports may impact the insurance coverage that the bundle recommendation engine 325 may recommend to the user. FIG. 6D shows an additional question related to past insurance consumption, and FIGS. 6E and 6F show additional questions related to the changes in the marital status of the insured. The user may advance through the questions by clicking the "Next" button or return to a previous question by clicking the "Back" button.

FIG. 6G shows an example user interface 640 that provides an example insurance recommendation report. FIG. 10 shows the full report that is shown in part on the user interface shown in FIG. 6G. The insurance bundle recommendation may be generated by the bundle recommendation engine 325. The recommendation pane 655 includes a list of insurance policies recommended to the user. Each entry includes dynamic scenario information that explains why the recommendations were made to the user. The dynamic scenario information is based on information collected from the user, the information obtained from third-party information sources, the claims and/or prescription information indicative of previous consumption of insurance, and/or other data analyzed by the bundle recommendation engine 325 to create the plan recommendation. The dynamic scenarios tie the explanations provided directly to this data. The dynamic scenarios may include costs and/or savings associated with each of the policy recommendations. The plan may include multiple types of insurance policies that provide a comprehensive insurance plan that provide the coverage for the user.

Figure 7:
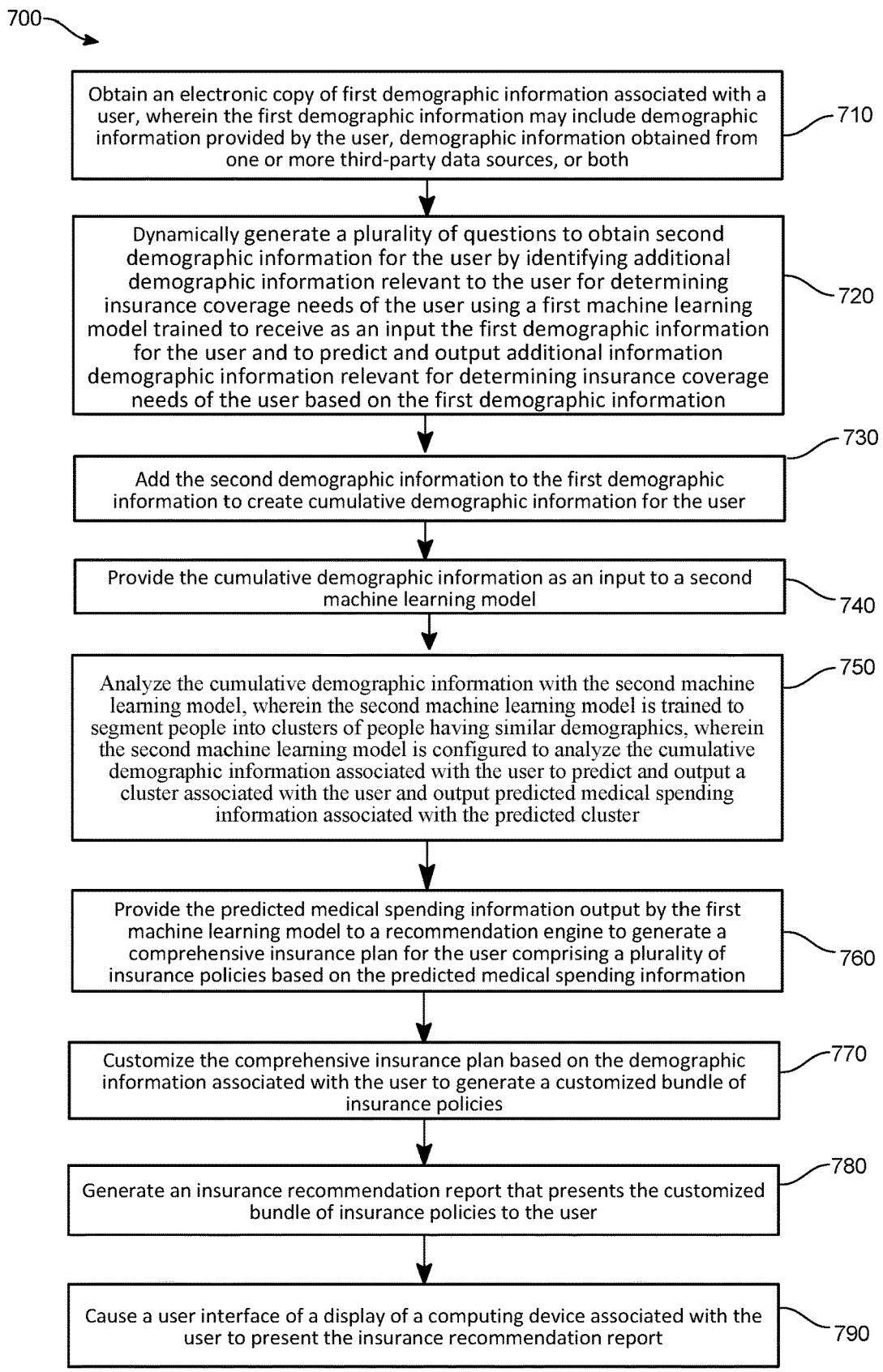
FIG. 7 is a flow chart of an example process for recommending a comprehensive bundle of insurance policies.

FIG. 7 illustrates a flow chart of an example process 700 for recommending a bundle of insurance policy to a user. The process 700 may be implemented by the CAAS 105 discussed in the preceding examples.

The process 700 may include an operation 710 of obtaining an electronic copy of first demographic information associated with a user. The first demographic information may include demographic information provided by the user, demographic information obtained from one or more third-party data sources, or both. As discussed in the preceding examples, the user demographic information may be collected from the user via the insurance questionnaire unit 330, from the third-party data providers 130, or both. The demographic information may include various information about the user, such as but not limited to, age, sex, race, and/or other information that may be used to segment the population into clusters of people having similar characteristics. The demographic information may include other factors associated with the user, such as but not limited to, past insurance claims information, medical history information, financial profile information, credit history information, family information, psychographics, interests, occupation, salary, physical activity, and other information that may be used to group users into clusters of people having similar characteristics.

The process 700 may include an operation 720 of dynamically generating a plurality of questions to obtain second demographic information for the user by identifying additional demographic information relevant to the user for determining insurance coverage needs of the user using a first machine learning model trained to receive as an input the first demographic information for the user and to predict and output additional information demographic information relevant for determining insurance coverage needs of the user based on the first demographic information. The insurance questionnaire unit 330 may analyze the first demographic information received from the user, the third-party data providers 130, or both to identify additional information that may be relevant for recommending a comprehensive insurance plan to the user. The insurance questionnaire unit 330 may identify gaps in first demographic information and generate questions to present to the user to fill in these gaps. The process of collecting and analyzing the demographic data obtained from the user, from the third-party data sources 130, or both and analyzing the data may be an iterative process that may be repeated multiple times as additional information about the user is obtained.

The process 700 may include an operation 730 of adding the second demographic information to the first demographic information to create cumulative demographic information for the user. The additional demographic information obtained for the user may be stored by the CAAS 105 and used by bundle recommendation engine 325 and/or other elements of the CAAS 105 to provide various services to the user.

The process 700 may include an operation 740 of providing the cumulative demographic information as an input to a second machine learning model and an operation 750 of analyzing the cumulative demographic information with the second machine learning model, wherein the first machine learning model is trained to segment people into clusters of people having similar demographics, wherein the first machine learning model is configured to analyze the cumulative demographic information associated with the user to predict a cluster associated with the user and output predicted medical spending information associated with the predicted cluster. The second machine learning model may be implemented by the cluster consumption prediction model 410 and may be trained to segment people into clusters of people having similar demographics. The second machine learning model may be configured to analyze the cumulative demographic data associated with the user to predict a cluster associated with the first user and output predicted medical spending information associated with the predicted cluster.

The process 700 may include an operation 760 of providing the predicted medical spending information output by the first machine learning model to a recommendation engine to generate a comprehensive insurance plan for the user comprising a plurality of insurance policies based on the predicted medical spending information. The bundle recommendation engine 325 may be configured to generate a comprehensive insurance plan for the user based on the predicted medical consumption obtained from the machine learning model as discussed in the preceding examples.

The process 700 may include an operation 770 of customizing the comprehensive insurance plan based on the demographic information associated with the user to generate a customized bundle of insurance policies. The bundle recommendation engine 325 may customize the comprehensive insurance plan according to the demographics of the user as discussed in the preceding examples.

The process 700 may include an operation 780 of generating an insurance recommendation report that presents the customized bundle of insurance policies to the user. The dynamic scenario unit 420 may present the recommended bundle of insurance policies in addition to dynamic scenario information that provides explanations tied to the user's information why each recommendation was made. An example of such a report is shown in FIG. 6G.

The process 700 may include an operation 790 of causing a user interface of a display of a computing device associated with the user to present the insurance recommendation report. The bundle recommendation engine 325 may cause the user's client device 115 to display the insurance recommendation report. As discussed in the preceding examples, the user may interact with the CAAS 105 via a native application associated with the CAAS 105 on the client device 115 or via a web browser on the client device 115. The recommended bundle of polices may be presented to the user. In some implementations, the CAAS 105 may be configured to provide a means for the user to obtain the recommended policies from the insurers.

The detailed examples of systems, devices, and techniques described in connection with FIGS. 1-7 are presented herein for illustration of the disclosure and its benefits. Such examples of use should not be construed to be limitations on the logical process embodiments of the disclosure, nor should variations of user interface methods from those described herein be considered outside the scope of the present disclosure. It is understood that references to displaying or presenting an item (such as, but not limited to, presenting an image on a display device, presenting audio via one or more loudspeakers, and/or vibrating a device)

include issuing instructions, commands, and/or signals causing, or reasonably expected to cause, a device or system to display or present the item. In some embodiments, various features described in FIGS. 1-7 are implemented in respective modules, which may also be referred to as, and/or include, logic, components, units, and/or mechanisms. Modules may constitute either software modules (for example, code embodied on a machine-readable medium) or hardware modules.

In some examples, a hardware module may be implemented mechanically, electronically, or with any suitable combination thereof. For example, a hardware module may include dedicated circuitry or logic that is configured to perform certain operations. For example, a hardware module may include a special-purpose processor, such as a field-programmable gate array (FPGA) or an Application Specific Integrated Circuit (ASIC). A hardware module may also include programmable logic or circuitry that is temporarily configured by software to perform certain operations and may include a portion of machine-readable medium data and/or instructions for such configuration. For example, a hardware module may include software encompassed within a programmable processor configured to execute a set of software instructions. It will be appreciated that the decision to implement a hardware module mechanically, in dedicated and permanently configured circuitry, or in temporarily configured circuitry (for example, configured by software) may be driven by cost, time, support, and engineering considerations.

Accordingly, the phrase "hardware module" should be understood to encompass a tangible entity capable of performing certain operations and may be configured or arranged in a certain physical manner, be that an entity that is physically constructed, permanently configured (for example, hardwired), and/or temporarily configured (for example, programmed) to operate in a certain manner or to perform certain operations described herein. As used herein, "hardware-implemented module" refers to a hardware module. Considering examples in which hardware modules are temporarily configured (for example, programmed), each of the hardware modules need not be configured or instantiated at any one instance in time. For example, where a hardware module includes a programmable processor configured by software to become a special-purpose processor, the programmable processor may be configured as respectively different special-purpose processors (for example, including different hardware modules) at different times. Software may accordingly configure a processor or processors, for example, to constitute a particular hardware module at one instance of time and to constitute a different hardware module at a different instance of time. A hardware module implemented using one or more processors may be referred to as being "processor implemented" or "computer implemented."

Hardware modules can provide information to, and receive information from, other hardware modules. Accordingly, the described hardware modules may be regarded as being communicatively coupled. Where multiple hardware modules exist contemporaneously, communications may be achieved through signal transmission (for example, over appropriate circuits and buses) between or among two or more of the hardware modules. In embodiments in which multiple hardware modules are configured or instantiated at different times, communications between such hardware modules may be achieved, for example, through the storage and retrieval of information in memory devices to which the multiple hardware modules have access. For example, one hardware module may perform an operation and store the output in a memory device, and another hardware module may then access the memory device to retrieve and process the stored output.

In some examples, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by, and/or among, multiple computers (as examples of machines including processors), with these operations being accessible via a network (for example, the Internet) and/or via one or more software interfaces (for example, an application program interface (API)). The performance of certain of the operations may be distributed among the processors, not only residing within a single machine, but deployed across several machines. Processors or processor-implemented modules may be in a single geographic location (for example, within a home or office environment, or a server farm), or may be distributed across multiple geographic locations.

Figure 8:
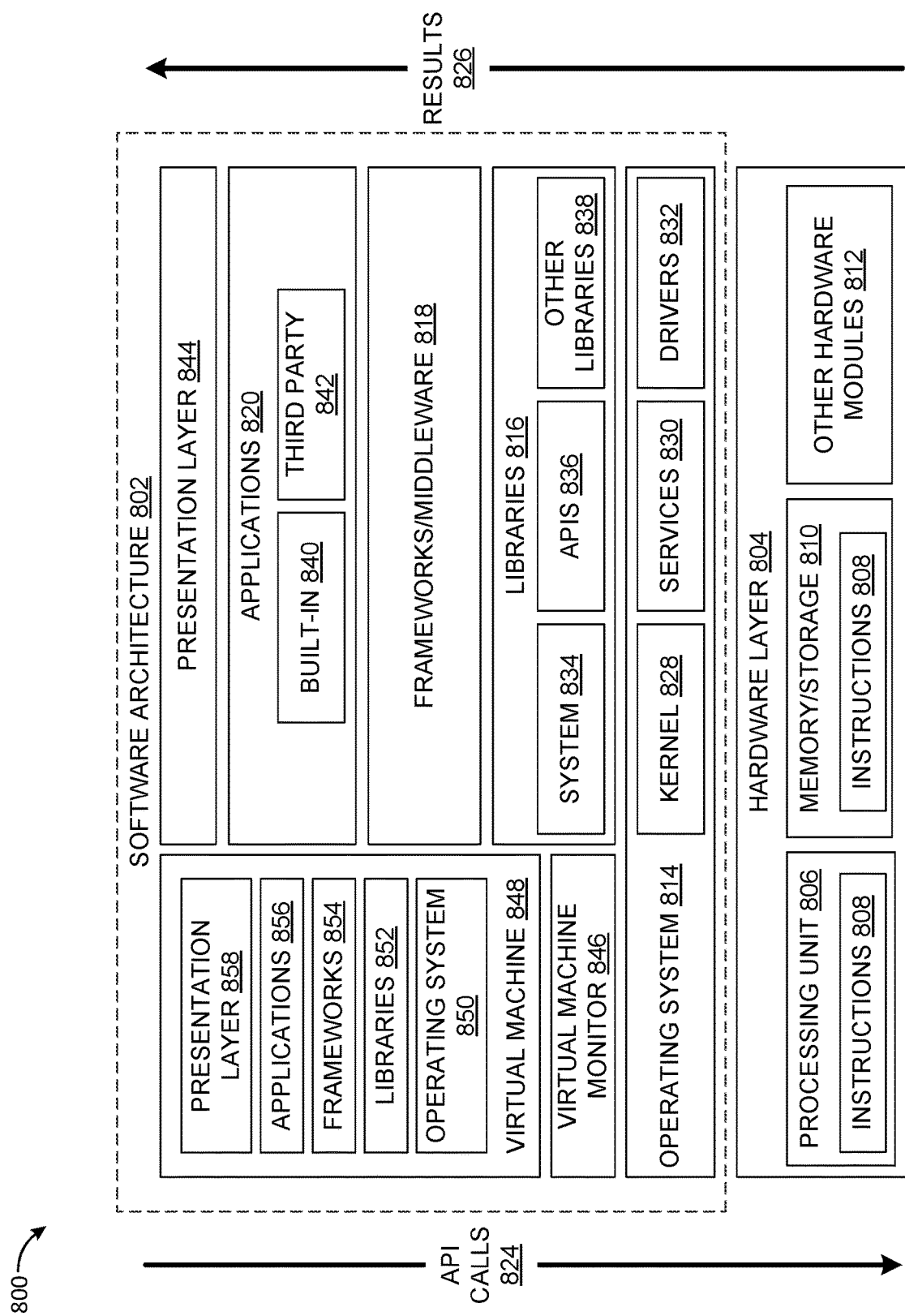
FIG. 8 is a block diagram showing an example software architecture, various portions of which may be used in conjunction with various hardware architectures herein described, which may implement any of the described features.

FIG. 8 is a block diagram 800 illustrating an example software architecture 802, various portions of which may be used in conjunction with various hardware architectures herein described, which may implement any of the above-described features. FIG. 8 is a non-limiting example of a software architecture, and it will be appreciated that many other architectures may be implemented to facilitate the functionality described herein. The software architecture 802 may execute on hardware such as a machine 900 of FIG. 9 that includes, among other things, processors 910, memory 930, and input/output (I/O) components 950. A representative hardware layer 804 is illustrated and can represent, for example, the machine 900 of FIG. 9. The representative hardware layer 804 includes a processing unit 806 and associated executable instructions 808. The executable instructions 808 represent executable instructions of the software architecture 802, including implementation of the methods, modules and so forth described herein. The hardware layer 804 also includes a memory/storage 810, which also includes the executable instructions 808 and accompanying data. The hardware layer 804 may also include other hardware modules 812. Instructions 808 held by processing unit 806 may be portions of instructions 808 held by the memory/storage 810.

The example software architecture 802 may be conceptualized as layers, each providing various functionality. For example, the software architecture 802 may include layers and components such as an operating system (OS) 814, libraries 816, frameworks 818, applications 820, and a presentation layer 844. Operationally, the applications 820 and/or other components within the layers may invoke API calls 824 to other layers and receive corresponding results 826. The layers illustrated are representative in nature and other software architectures may include additional or different layers. For example, some mobile or special purpose operating systems may not provide the frameworks/middleware 818.

The OS 814 may manage hardware resources and provide common services. The OS 814 may include, for example, a kernel 828, services 830, and drivers 832. The kernel 828 may act as an abstraction layer between the hardware layer 804 and other software layers. For example, the kernel 828 may be responsible for memory management, processor management (for example, scheduling), component management, networking, security settings, and so on. The services 830 may provide other common services for the other software layers. The drivers 832 may be responsible for controlling or interfacing with the underlying hardware layer 804. For instance, the drivers 832 may include display drivers, camera drivers, memory/storage drivers, peripheral device drivers (for example, via Universal Serial Bus (USB)), network and/or wireless communication drivers, audio drivers, and so forth depending on the hardware and/or software configuration.

The libraries 816 may provide a common infrastructure that may be used by the applications 820 and/or other components and/or layers. The libraries 816 typically provide functionality for use by other software modules to perform tasks, rather than rather than interacting directly with the OS 814. The libraries 816 may include system libraries 834 (for example, C standard library) that may provide functions such as memory allocation, string manipulation, file operations. In addition, the libraries 816 may include API libraries 836 such as media libraries (for example, supporting presentation and manipulation of image, sound, and/or video data formats), graphics libraries (for example, an OpenGL library for rendering 2D and 3D graphics on a display), database libraries (for example, SQLite or other relational database functions), and web libraries (for example, WebKit that may provide web browsing functionality). The libraries 816 may also include a wide variety of other libraries 838 to provide many functions for applications 820 and other software modules.

The frameworks 818 (also sometimes referred to as middleware) provide a higher-level common infrastructure that may be used by the applications 820 and/or other software modules. For example, the frameworks 818 may provide various graphic user interface (GUI) functions, high-level resource management, or high-level location services. The frameworks 818 may provide a broad spectrum of other APIs for applications 820 and/or other software modules.

The applications 820 include built-in applications 840 and/or third-party applications 842. Examples of built-in applications 840 may include, but are not limited to, a contacts application, a browser application, a location application, a media application, a messaging application, and/or a game application. Third-party applications 842 may include any applications developed by an entity other than the vendor of the particular platform. The applications 820 may use functions available via OS 814, libraries 816, frameworks 818, and presentation layer 844 to create user interfaces to interact with users.

Some software architectures use virtual machines, as illustrated by a virtual machine 848. The virtual machine 848 provides an execution environment where applications/modules can execute as if they were executing on a hardware machine (such as the machine 900 of FIG. 9, for example). The virtual machine 848 may be hosted by a host OS (for example, OS 814) or hypervisor, and may have a virtual machine monitor 846 which manages operation of the virtual machine 848 and interoperation with the host operating system. A software architecture, which may be different from software architecture 802 outside of the virtual machine, executes within the virtual machine 848 such as an OS 850, libraries 852, frameworks 854, applications 856, and/or a presentation layer 858.

Figure 9:
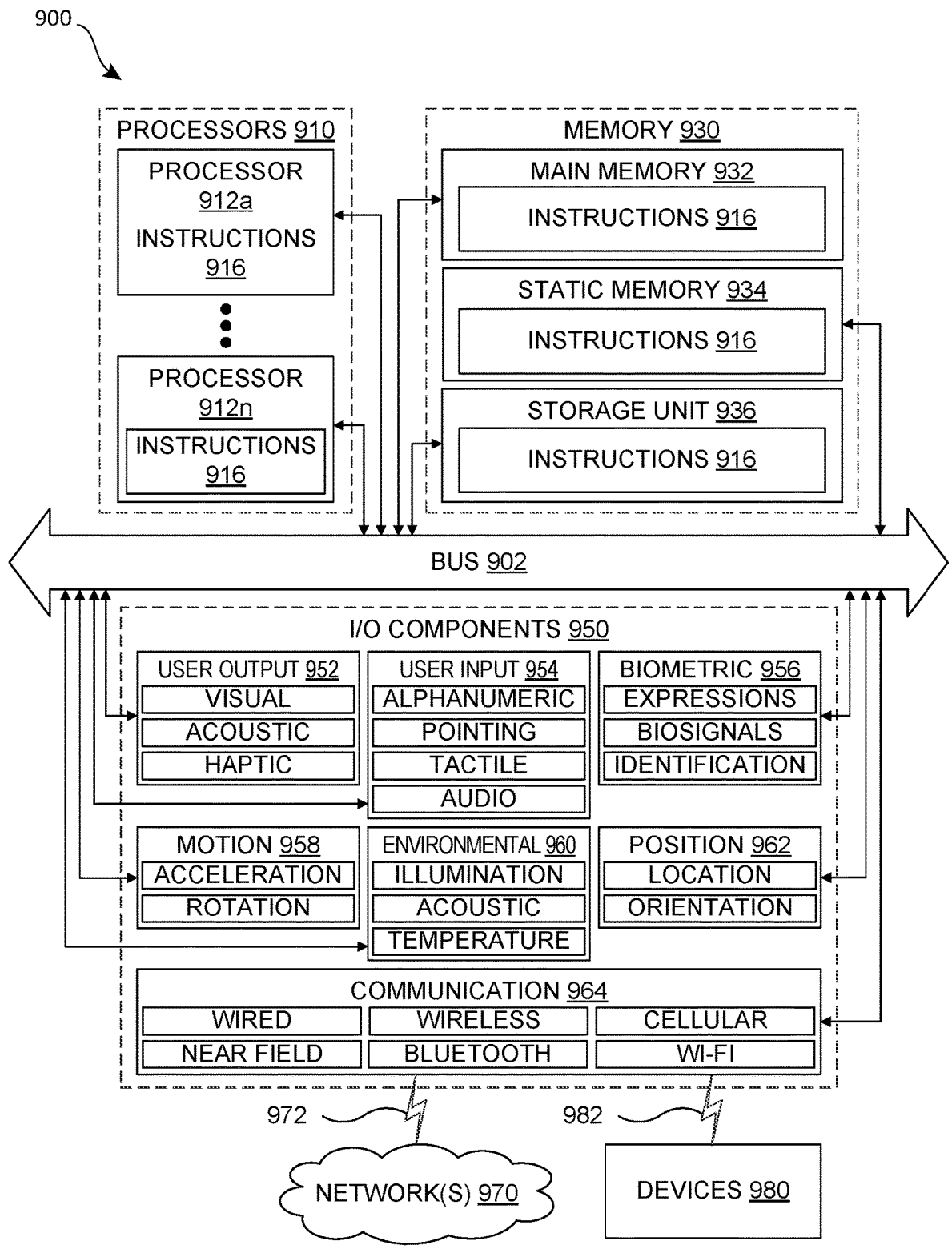
FIG. 9 is a block diagram showing components of an example machine configured to read instructions from a machine-readable medium and perform any of the features described herein.

FIG. 9 is a block diagram illustrating components of an example machine 900 configured to read instructions from a machine-readable medium (for example, a machine-readable storage medium) and perform any of the features described herein. The example machine 900 is in a form of a computer system, within which instructions 916 (for example, in the form of software components) for causing the machine 900 to perform any of the features described herein may be executed. As such, the instructions 916 may be used to implement modules or components described herein. The instructions 916 cause unprogrammed and/or unconfigured machine 900 to operate as a particular machine configured to carry out the described features. The machine 900 may be configured to operate as a standalone device or may be coupled (for example, networked) to other machines. In a networked deployment, the machine 900 may operate in the capacity of a server machine or a client machine in a server-client network environment, or as a node in a peer-to-peer or distributed network environment. Machine 900 may be embodied as, for example, a server computer, a client computer, a personal computer (PC), a tablet computer, a laptop computer, a netbook, a set-top box (STB), a gaming and/or entertainment system, a smart phone, a mobile device, a wearable device (for example, a smart watch), and an Internet of Things (IoT) device. Further, although only a single machine 900 is illustrated, the term "machine" includes a collection of machines that individually or jointly execute the instructions 916.

The machine 900 may include processors 910, memory 930, and I/O components 950, which may be communicatively coupled via, for example, a bus 902. The bus 902 may include multiple buses coupling various elements of machine 900 via various bus technologies and protocols. In an example, the processors 910 (including, for example, a central processing unit (CPU), a graphics processing unit (GPU), a digital signal processor (DSP), an ASIC, or a suitable combination thereof) may include one or more processors 912a to 912n that may execute the instructions 916 and process data. In some examples, one or more processors 910 may execute instructions provided or identified by one or more other processors 910. The term "processor" includes a multi-core processor including cores that may execute instructions contemporaneously. Although FIG. 9 shows multiple processors, the machine 900 may include a single processor with a single core, a single processor with multiple cores (for example, a multi-core processor), multiple processors each with a single core, multiple processors each with multiple cores, or any combination thereof. In some examples, the machine 900 may include multiple processors distributed among multiple machines.

The memory/storage 930 may include a main memory 932, a static memory 934, or other memory, and a storage unit 936, both accessible to the processors 910 such as via the bus 902. The storage unit 936 and memory 932, 934 store instructions 916 embodying any one or more of the functions described herein. The memory/storage 930 may also store temporary, intermediate, and/or long-term data for processors 910. The instructions 916 may also reside, completely or partially, within the memory 932, 934, within the storage unit 936, within at least one of the processors 910 (for example, within a command buffer or cache memory), within memory at least one of I/O components 950, or any suitable combination thereof, during execution thereof. Accordingly, the memory 932, 934, the storage unit 936, memory in processors 910, and memory in I/O components 950 are examples of machine-readable media.

As used herein, "machine-readable medium" refers to a device able to temporarily or permanently store instructions and data that cause machine 900 to operate in a specific fashion, and may include, but is not limited to, random-access memory (RAM), read-only memory (ROM), buffer memory, flash memory, optical storage media, magnetic storage media and devices, cache memory, network-accessible or cloud storage, other types of storage and/or any suitable combination thereof. The term "machine-readable medium" applies to a single medium, or combination of multiple media, used to store instructions (for example, instructions 916) for execution by a machine 900 such that the instructions, when executed by one or more processors 910 of the machine 900, cause the machine 900 to perform and one or more of the features described herein. Accordingly, a "machine-readable medium" may refer to a single storage device, as well as "cloud-based" storage systems or storage networks that include multiple storage apparatus or devices. The term "machine-readable medium" excludes signals per se.

The I/O components 950 may include a wide variety of hardware components adapted to receive input, provide output, produce output, transmit information, exchange information, capture measurements, and so on. The specific I/O components 950 included in a particular machine will depend on the type and/or function of the machine. For example, mobile devices such as mobile phones may include a touch input device, whereas a headless server or IoT device may not include such a touch input device. The particular examples of I/O components illustrated in FIG. 9 are in no way limiting, and other types of components may be included in machine 900. The grouping of I/O components 950 are merely for simplifying this discussion, and the grouping is in no way limiting. In various examples, the I/O components 950 may include user output components 952 and user input components 954. User output components 952 may include, for example, display components for displaying information (for example, a liquid crystal display (LCD) or a projector), acoustic components (for example, speakers), haptic components (for example, a vibratory motor or force-feedback device), and/or other signal generators. User input components 954 may include, for example, alphanumeric input components (for example, a keyboard or a touch screen), pointing components (for example, a mouse device, a touchpad, or another pointing instrument), and/or tactile input components (for example, a physical button or a touch screen that provides location and/or force of touches or touch gestures) configured for receiving various user inputs, such as user commands and/or selections.

In some examples, the I/O components 950 may include biometric components 956, motion components 958, environmental components 960, and/or position components 962, among a wide array of other physical sensor components. The biometric components 956 may include, for example, components to detect body expressions (for example, facial expressions, vocal expressions, hand or body gestures, or eye tracking), measure biosignals (for example, heart rate or brain waves), and identify a person (for example, via voice-, retina-, fingerprint-, and/or facial-based identification). The motion components 958 may include, for example, acceleration sensors (for example, an accelerometer) and rotation sensors (for example, a gyroscope). The environmental components 960 may include, for example, illumination sensors, temperature sensors, humidity sensors, pressure sensors (for example, a barometer), acoustic sensors (for example, a microphone used to detect ambient noise), proximity sensors (for example, infrared sensing of nearby objects), and/or other components that may provide indications, measurements, or signals corresponding to a surrounding physical environment. The position components 962 may include, for example, location sensors (for example, a Global Position System (GPS) receiver), altitude sensors (for example, an air pressure sensor from which altitude may be derived), and/or orientation sensors (for example, magnetometers).

The I/O components 950 may include communication components 964, implementing a wide variety of technologies operable to couple the machine 900 to network(s) 970 and/or device(s) 980 via respective communicative couplings 972 and 982. The communication components 964 may include one or more network interface components or other suitable devices to interface with the network(s) 970. The communication components 964 may include, for example, components adapted to provide wired communication, wireless communication, cellular communication, Near Field Communication (NFC), Bluetooth communication, Wi-Fi, and/or communication via other modalities. The device(s) 980 may include other machines or various peripheral devices (for example, coupled via USB).

In some examples, the communication components 964 may detect identifiers or include components adapted to detect identifiers. For example, the communication components 964 may include Radio Frequency Identification (RFID) tag readers, NFC detectors, optical sensors (for example, one- or multi-dimensional bar codes, or other optical codes), and/or acoustic detectors (for example, microphones to identify tagged audio signals). In some examples, location information may be determined based on information from the communication components 964, such as, but not limited to, geo-location via Internet Protocol (IP) address, location via Wi-Fi, cellular, NFC, Bluetooth, or other wireless station identification and/or signal triangulation.

While various embodiments have been described, the description is intended to be exemplary, rather than limiting, and it is understood that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus, the following claims are hereby incorporated into the Detailed Description, with each claim standing on its own as a separately claimed subject matter.

What is claimed is:

1. A data processing system comprising:
    a processor; and
    a machine-readable medium storing executable instructions that, when executed, cause the processor to perform operations comprising:
        obtaining an electronic copy of first demographic information associated with a user;
        providing the first demographic information as an input to a first machine learning model;
        analyzing the first demographic information with the first machine learning model, the first machine learning model being trained using demographic information and claims information to cluster people into clusters having similar demographics and having similar medical spending, the first machine model outputting a predicted cluster and predicted medical spending information for the user;
        providing the predicted medical spending information to a recommendation engine to generate a customized comprehensive insurance plan for the user comprising a plurality of insurance policies based on the predicted medical spending information;
        generating an insurance recommendation report that presents the customized comprehensive insurance plan to the user; and
        causing a user interface of a display of a computing device associated with the user to present the insurance recommendation report.

2. The data processing system of claim 1, the machine-readable medium includes instructions configured to cause the processor to perform:
    customizing the comprehensive insurance plan based on the first demographic information associated with the user to generate a customized bundle of insurance policies; and
    presenting the customized bundle of insurance policies in the insurance recommendation report.

3. The data processing system of claim 2, wherein generating the insurance recommendation report further comprises:
    obtaining a description of each insurance policy including the bundle of insurance policies;
    generating a narrative indicating why each insurance policy including in the bundle of insurance policies has been selected for the user; and
    generating the insurance recommendation report to present the narrative and the description of each insurance policy.

4. The data processing system of claim 2, wherein the machine-readable medium includes instructions configured to cause the processor to perform:
    causing a user interface of a display of a computing device associated with the user to present a policy procurement user interface, the policy procurement user interface configured to guide the user through obtaining one or more policies included in the customized bundle of insurance policies.

5. The data processing system of claim 1, wherein the predicted medical spending information includes a predicted amount spent on medical claims and types of claims typically filed by people associated with the predicted cluster.

6. The data processing system of claim 1, the machine-readable medium includes instructions configured to cause the processor to perform:
    dynamically generating a plurality of questions to obtain second demographic information for the user by identifying additional demographic information relevant to the user for determining insurance coverage needs of the user using a second machine learning model, the second machine learning model trained to receive as an input the first demographic information for the user and to predict and output additional information demographic information relevant for determining insurance coverage needs of the user based on the first demographic information;
    obtaining the second demographic information as responses to the plurality of questions; and
    combining the second demographic information with the first demographic information before providing the first demographic information as an input to the first machine learning model.

7. The data processing system of claim 6, wherein the policy procurement user interface also guides the user through modifying one or more existing policies based on the customized bundle of insurance policies.

8. A method implemented in a data processing system for recommending insurance plans, the method comprising:
obtaining an electronic copy of first demographic information associated with a user;
providing the first demographic information as an input to a first machine learning model;
analyzing the first demographic information with the first machine learning model, the first machine learning model being trained using demographic information and claims information to cluster people into clusters having similar demographics and having similar medical spending, the first machine model outputting a predicted cluster and predicted medical spending information for the user;
providing the predicted medical spending information to a recommendation engine to generate a customized comprehensive insurance plan for the user comprising a plurality of insurance policies based on the predicted medical spending information;
generating an insurance recommendation report that presents the customized comprehensive insurance plan to the user; and
causing a user interface of a display of a computing device associated with the user to present the insurance recommendation report.

9. The method of claim 8, further comprising:
customizing the comprehensive insurance plan based on the first demographic information associated with the user to generate a customized bundle of insurance policies; and
presenting the customized bundle of insurance policies in the insurance recommendation report.

10. The method of claim 8, wherein generating the insurance recommendation report further comprises:
obtaining a description of each insurance policy including the bundle of insurance policies;
generating a narrative indicating why each insurance policy including in the bundle of insurance policies has been selected for the user; and
generating the insurance recommendation report to present the narrative and the description of each insurance policy.

11. The method of claim 8, further comprising:
causing a user interface of a display of a computing device associated with the user to present a policy procurement user interface, the policy procurement user interface configured to guide the user through obtaining one or more policies included in the customized bundle of insurance policies.

12. The method of claim 8, wherein the predicted medical spending information includes a predicted amount spent on medical claims and types of claims typically filed by people associated with the predicted cluster.

13. The method of claim 8, further comprising:
dynamically generating a plurality of questions to obtain second demographic information for the user by identifying additional demographic information relevant to the user for determining insurance coverage needs of the user using a second machine learning model, the second machine learning model trained to receive as an input the first demographic information for the user and to predict and output additional information demographic information relevant for determining insurance coverage needs of the user based on the first demographic information;
obtaining the second demographic information as responses to the plurality of questions; and
combining the second demographic information with the first demographic information before providing the first demographic information as an input to the first machine learning model.

14. The method of claim 13, wherein the policy procurement user interface also guides the user through modifying one or more existing policies based on the customized bundle of insurance policies.

15. A machine-readable medium on which are stored instructions that, when executed, cause a processor of a programmable device to perform operations of:
obtaining an electronic copy of first demographic information associated with a user;
providing the first demographic information as an input to a first machine learning model;
analyzing the first demographic information with the first machine learning model, the first machine learning model being trained using demographic information and claims information to cluster people into clusters having similar demographics and having similar medical spending, the first machine model outputting a predicted cluster and predicted medical spending information for the user;
providing the predicted medical spending information to a recommendation engine to generate a customized comprehensive insurance plan for the user comprising a plurality of insurance policies based on the predicted medical spending information;
generating an insurance recommendation report that presents the customized comprehensive insurance plan to the user; and
causing a user interface of a display of a computing device associated with the user to present the insurance recommendation report.

16. The machine-readable medium of claim 15, the machine-readable medium further comprising instructions configured to cause the processor to perform operations of:
customizing the comprehensive insurance plan based on the first demographic information associated with the user to generate a customized bundle of insurance policies; and
presenting the customized bundle of insurance policies in the insurance recommendation report.

17. The machine-readable medium of claim 16, wherein generating the insurance recommendation report further comprises:
obtaining a description of each insurance policy including the bundle of insurance policies;
generating a narrative indicating why each insurance policy including in the bundle of insurance policies has been selected for the user; and
generating the insurance recommendation report to present the narrative and the description of each insurance policy.

18. The machine-readable medium of claim 16, wherein the machine-readable medium includes instructions configured to cause the processor to perform:
causing a user interface of a display of a computing device associated with the user to present a policy procurement user interface, the policy procurement user interface configured to guide the user through obtaining one or more policies included in the customized bundle of insurance policies.

19. The machine-readable medium of claim 15, wherein the predicted medical spending information includes a predicted amount spent on medical claims and types of claims typically filed by people associated with the predicted cluster.

20. The machine-readable medium of claim 15, the machine-readable medium includes instructions configured to cause the processor to perform:
- dynamically generating a plurality of questions to obtain second demographic information for the user by identifying additional demographic information relevant to the user for determining insurance coverage needs of the user using a second machine learning model, the second machine learning model trained to receive as an input the first demographic information for the user and to predict and output additional information demographic information relevant for determining insurance coverage needs of the user based on the first demographic information;
- obtaining the second demographic information as responses to the plurality of questions; and
- combining the second demographic information with the first demographic information before providing the first demographic information as an input to the first machine learning model.

* * * * *